US012629407B2

(12) United States Patent
Charych et al.

(10) Patent No.: US 12,629,407 B2
(45) Date of Patent: May 19, 2026

(54) CONJUGATES OF AN IL-7 MOIETY AND A POLYMER

(71) Applicant: Nektar Therapeutics, San Francisco, CA (US)

(72) Inventors: Deborah H. Charych, Albany, CA (US); Ping Zhang, Millbrae, CA (US); Peter Benedict Kirk, San Mateo, CA (US)

(73) Assignee: Nektar Therapeutics, San Francisco, CA (US)

( * ) Notice: Subject to any disclaimer, the term of this patent is extended or adjusted under 35 U.S.C. 154(b) by 144 days.

(21) Appl. No.: 15/556,996

(22) PCT Filed: Mar. 11, 2016

(86) PCT No.: PCT/US2016/022146

§ 371 (c)(1),
(2) Date: Sep. 8, 2017

(87) PCT Pub. No.: WO2016/145388

PCT Pub. Date: Sep. 15, 2016

(65) Prior Publication Data

US 2019/0290733 A1 Sep. 26, 2019

Related U.S. Application Data

(60) Provisional application No. 62/131,634, filed on Mar. 11, 2015.

(51) Int. Cl.

| | |
|---|---|
| ***A61K 38/20*** | (2006.01) |
| ***A61K 47/60*** | (2017.01) |
| ***C07K 14/54*** | (2006.01) |

(52) U.S. Cl.

CPC .......... *A61K 38/2046* (2013.01); *A61K 47/60* (2017.08); *C07K 14/5418* (2013.01)

(58) Field of Classification Search

CPC . A61K 38/2046; A61K 47/60; C07K 14/5418
See application file for complete search history.

(56) References Cited

U.S. PATENT DOCUMENTS

| | | | | |
|---|---|---|---|---|
| 5,739,208 | A | 4/1998 | Harris | |
| 5,932,462 | A | 8/1999 | Harris et al. | |
| 6,177,079 | B1 | 1/2001 | Grabstein et al. | |
| 7,589,179 | B2 | 9/2009 | Gillies et al. | |
| 7,956,032 | B2 | 6/2011 | Defrees et al. | |
| 2004/0136952 | A1 | 7/2004 | Bhaskaran et al. | |
| 2005/0014903 | A1 | 1/2005 | Kozlowski et al. | |
| 2005/0249701 | A1 * | 11/2005 | Morre | A61P 31/04 424/85.2 |
| 2006/0141581 | A1 | 6/2006 | Gillies et al. | |
| 2006/0293499 | A1 | 12/2006 | Bentley et al. | |
| 2014/0328791 | A1 | 11/2014 | Bossard et al. | |

FOREIGN PATENT DOCUMENTS

| | | | | |
|---|---|---|---|---|
| CN | 102145178 B * | 9/2012 | | |
| WO | WO 90/12874 A2 | 11/1990 | | |
| WO | WO 99/45964 A1 | 9/1999 | | |
| WO | WO 01/62827 A2 | 8/2001 | | |
| WO | WO 02/085300 A2 | 10/2002 | | |
| WO | WO 03/044056 A2 | 5/2003 | | |
| WO | WO 2004/060300 A2 | 7/2004 | | |
| WO | WO 2008/106186 A2 | 9/2008 | | |
| WO | WO-2012065086 A1 * | 5/2012 | A61K 38/2013 | |
| WO | WO 2013/020079 A2 | 2/2013 | | |

OTHER PUBLICATIONS

Eliason, J.F., Pegylated Cytokines—Potential Application in Immunotherapy of Cancer. BioDrugs. 2001; 15(11):705-11.*

Bansal et al., PEGylation improves pharmacokinetic profile, liver uptake and efficacy of Interferon gamma in liver fibrosis. J Control Release. Sep. 25, 2011;154(3):233-40.*

Mattos et al., PEGylation of interleukin-10 improves the pharmacokinetic profile and enhances the antifibrotic effectivity in CCI4-induced fibrogenesis in mice. J Control Release. Aug. 20, 2012;162(1):84-91.*

Cheng et al. Analytical Measurement of PEGylated Molecules. Bioconjug Chem. May 16, 2012;23(5):881-99.*

J. Kling, PEGylation of Biologics. Bioprocess International, Mar. 1, 2013.*

Fischer et al., "Recombinant human acetylcholinesterase expressed in *Escherichia coli*: refolding, purification and characterization", Biotechnol. Appl. Biochem., vol. 21 pp. 295-311, (1995).

Fry et al., "Interleukin-7 restores immunity in athymic T-cell-depleted hosts", Blood, vol. 97, pp. 1525-1533, (2001).

Ghazawi et al., "IL-7 downregulates IL-7Rα expression in human CD8 T cells by two independent mechanisms", Immunology and Cell Biology, vol. 91, pp. 149-158, (2013).

Heldt et al., "The Use of Glycidol to Introduce Aldehyde Functions Into Proteins-Application to the Fluorescent Labelling of Bovine Serum Albumin and Avidin", Eur. J. Org. Chem., pp. 5429-5433, (2007).

Komschiles et al., "Diverse immunological and hematological effects of interleukin 7: implications for clinical application", Journal of Leukocyte Biology, vol. 58, pp. 623-633, (Dec. 1995).

Kroemer et al., "Comparison of the 3D models fo four different human IL-7 isoforms with human and murine IL-7", Protein Engineering, vol. 11, No. 1, pp. 31-40, (1998).

Kroemer et al., "Homology modeling study of the human interleukin-7 receptor complex", Protein Engineering, vol. 9, No. 12, pp. 1135-1142, (1996).

(Continued)

*Primary Examiner* — Ruixiang Li
(74) *Attorney, Agent, or Firm* — Jacqueline F. Mahoney; Susan T. Evans

(57) ABSTRACT

Conjugates of an IL-7 moiety and one or more nonpeptidic, water-soluble polymers are provided. Typically, the non-peptidic, water-soluble polymer is poly(ethylene glycol) or a derivative thereof. Also provided, among other things, are compositions comprising conjugates, methods of making conjugates, and methods of administering compositions to an individual.

11 Claims, 3 Drawing Sheets

Specification includes a Sequence Listing.

(56) References Cited

OTHER PUBLICATIONS

Kronman et al., "Production and secretion of high levels of recombinant human acetylcholinesterase in cultured cell lines: microheterogeneity of the catalytic subunit", Gene, vol. 121, pp. 295-304, (1992).
Li et al., "Recombinant IL-7 enhances the potency of GM-CSF-secreting tumor cell immunotherapy", Clinical Immunology, vol. 123, pp. 155-165, (2007).
Luchansky et al., "Metabolic Functionalization of Recombinant Glycoproteins", Biochemistry, vol. 43, pp. 12358-12366, (2004).
Mackall et al., "IL-7 increases both thymic-dependent and thymic-independent T-cell regeneration after bone marrow transplantation", Blood, vol. 97, pp. 1491-1497, (2001).
Markley et al., "IL-7 and IL-21 are superior to IL-2 and IL-15 in promoting human T cell-mediated rejection of systemic lymphoma in immunodeficient mice", Blood, vol. 115, No. 17, pp. 3508-3519, (2010).
Mor et al., "Expression of Recombinant Human Acetylcholinesterase in Transgenic Tomato Plants", Biotechnol. Bioeng., vol. 75, pp. 259-266, (2001).
Morel et al., "Expression and processing of vertebrate acetylcholinesterase in the yeast *Pichia pastoris*", Biochem. J., vol. 328, pp. 121-129, (1997).
Morrissey et al., "Administration of IL-7 to Mice with Cyclophosphamide-Induced Lymphopenia Accelerates Lymphocyte Repopulation", The Journal Of Immunology, vol. 146, No. 5, pp. 1547-1552, (Mar. 1, 1991).
Nam et al., "Marked enhancement of antigen-specific T-cell responses by IL-7-fused nonlytic, but not lytic, Fc as a genetic adjuvant", Eur. J. Immunol., vol. 40, pp. 351-358, (2010).
Namen et al., "B Cell Precursor Growth-Promoting Activity", J. Exp. Med., vol. 167, pp. 988-1002, (Mar. 1988).
Ouchi et al., "Design of Antitumor Agent-Terminated Poly(Ethylene Glycol) Conjugate as Macromolecular Prodrug", Polymer Preprints, vol. 38, No. 1, pp. 582-583, (1997).
Ouellette et al., "Production and purification of refolded recombinant human IL-7 from inclusion bodies", Protein Expression and Purification, vol. 30, pp. 156-166, (2003).
Sims et al., "A Method for the Estimation of Polyethylene Glycol in Plasma Protein Fractions", Analytical Biochemistry, vol. 107, pp. 60-63, (1980).
Storek et al., "Interleukin-7 improves CD4 T-cell reconstitution after autologous CD34 cell transplantation in monkeys", Blood, vol. 101, pp. 4209-4218, (2003).
Tang et al., "IL-7 inhibits tumor growth by promoting T cell-mediated antitumor immunity in Meth A model", Immunology Letters, vol. 158, pp. 159-166, (2014).
Vudattu et al., "Expression analysis and functional activity of interleukin-7 splice variants", Genes and Immunity, vol. 10, pp. 132-140, (2009).
Wong et al., "The IL-15-based superagonist ALT-803 promotes the antigen-independent conversion of memory $CD8^+$ T cells into innate-like effector cells with antitumor activity", OncoImmunology, vol. 2, No. 11, pp. e26442-1-e25442-3, (Nov. 2013).
Zalipsky, "Chemistry of polyethylene glycol conjugates with biologically active molecules", Advanced Drug Delivery Reviews, vol. 16, pp. 157-182, (1995).
Zalipsky et al., "Use of Functionalized Poly(Ethylene Glycol)s for Modification of Polypeptides", Poly(Ethylene Glycol) Chemistry: Biotechnical and Biomedical Applications, edited by J. Milton Harris, Plenum Press, New York, 347-370, (1992).
Zustiak et al., "Hydrolytically Degradable Poly(Ethylene Glycol) Hydrogel Scaffolds with Tunable Degradation and Mechanical Properties", Biomacromolecules, vol. 11, pp. 1348-1457, (2010).
PCT International Search Report and the Written Opinion corresponding to PCT Application No. PCT/US2016/022146 date of mailing Jul. 18, 2016.
PCT International Preliminary Report on Patentability corresponding to PCT Application No. PCT/US2016/022146 date of mailing Sep. 21, 2017.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003—$1^{st}$, (Jan. 2003).
NOF Corporation, PEG Derivatives, Phospholipid and Drug Delivery Materials for Pharmaceuticals, 27 pages, Catalogue 2003—$2^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
Australian First Examination Report corresponding to Australian Patent Application No. 2016228555 date of report Dec. 14, 2020.
English Translation of the Notification of the First Office Action corresponding to Chinese Patent Application No. 20168001816.7 date of notification Sep. 2, 2020.
English Translation of the Notice of Final Rejection corresponding to Japanese Patent Application No. 2017-547157 mailing date Oct. 30, 2020.
English Translation of the $1^{st}$ Substantive Examination corresponding to Mexican Patent Application No. MX/a/2017/011562 dated Oct. 9, 2020.
European Communication corresponding to European Patent Application No. 16762659.7 dated Jul. 6, 2018.
European Communication corresponding to European Patent Application No. 16762659.7 dated Jun. 25, 2019.
European Communication corresponding to European Patent Application No. 16762659.7 dated Jun. 16, 2020.
English Translation of Israel Examination Report corresponding to Israel Patent Application No. 201747031687 dated Jan. 30, 2020.
English Translation of Japanese Notice of Reasons for Rejection corresponding to Japanese Patent Application No. 2017-547157 mailing date Dec. 26, 2019.
English Translation of Chinese Notification of Second Office Action corresponding to Chinese Patent Application No. 201680014816.7 date of notification Jun. 11, 2021.

(56) References Cited

OTHER PUBLICATIONS

English Translation of Indian Examination Report corresponding to Indian Patent Application No. 201747031687 date of dispatch Jan. 30, 2020.
English Translation of $2^{nd}$ Substantive Examination Requirements corresponding to Mexican Patent Application No. MX/a/2017/011562 dated May 18, 2021.
Katzman et al., "Opposing functions of IL-2 and IL-7 in the regulation of immune responses", Cytokine, Vo. 56, pp. 116-121, (2011).
Verhoef et al., "Questioning the Use of PEGylation for Drug Delivery", Drug Deliv. Transl. Rev., vol. 3, No. 6, pp. 499-503, (Dec. 2013).
Canadian Office Action corresponding to Canadian Patent Application No. 2,978,330 dated Jun. 9, 2022.
Canadian Office Action corresponding to Canadian Patent Application No. 2,978,330 dated Feb. 10, 2023.
English Translation of Chinese Rejection Decision corresponding to Chinese Patent Application No. 201680014816.7 date of notification Jan. 20, 2022.
European Communication corresponding to European Patent Application No. 16 762 659.7 dated Mar. 14, 2022.
English Translation of Japanese Notice of Reasons for Rejection corresponding to Japanese Patent Application No. 2022-129624 mailing date Jul. 24, 2023.

* cited by examiner

1: Mark 12 molecular weight standard;
2: Native IL-7; 3: mPEG2-40K-IL-7,10X
4: mPEG2-40K-IL-7,20X
5: mPEG2-40K-IL-7,50X 1: native IL-7; 2: C2-20K-IL-7,10X
3: C2-20K-IL-7,20X
4 &5: C2-20K-IL-7,50X
6: Mark 12 molecular weight standard

CONJUGATES OF AN IL-7 MOIETY AND A POLYMER

CROSS REFERENCE TO RELATED APPLICATION

This application is a 35 U.S.C. § 371 application of International Application No. PCT/US2016/022146, filed Mar. 11, 2016, designating the United States, which claims the benefit of priority under 35 U.S.C. § 119(e) to U.S. Provisional Patent Application No. 62/131,634, filed Mar. 11, 2015, the disclosure of which is incorporated herein by reference in its entirety.

REFERENCE TO A SEQUENCE LISTING SUBMITTED VIA EFS-WEB

The contents of the ASCII text file of the sequence listing named, “SHE0517_00_SL.txt”, having a size of 9003 bytes, created Aug. 16, 2018 and filed via EFS-WEB on Feb. 6, 2019, is incorporated herein by reference in its entirety.

FIELD

Among other things, one or more embodiments of the present invention relate generally to conjugates comprising an IL-7 moiety (i.e., a moiety having at least some activity similar to human IL-7) and a water-soluble, non-peptidic polymer. In addition, the invention relates to (among other things) compositions comprising conjugates, methods for synthesizing conjugates, and methods of administering a composition.

BACKGROUND

Cytokines are stimulators of the immune system and are thus useful as drugs. For example, interferon-alpha (IFN-α), interferon-beta (IFN-β), interleukin-2 (IL-2), and granulocyte/macrophage-colony stimulating factor (GM-CSF) are all approved drugs. Drugs in this class are used to treat individuals suffering from viral infections, cancer, and immune system misregulation such as autoimmune disease, and to promote recovery of the immune system after cancer chemotherapy. Unfortunately, these proteins can stimulate an immune response against themselves, causing patients to develop antibodies against the therapeutic protein. These antibodies can also inhibit function of the same protein endogenously produced within the patient, resulting in potential long-term consequences for patient health.

Interleukin-7 (“IL-7”) is a cytokine that promotes survival and/or proliferation of T-cells, long term memory T cells, B-cells, and other immune cells. This cytokine binds to the IL-7 receptor, which is a cell surface protein and is made up of two different smaller protein chains (i.e., IL-7 receptor-alpha and common gamma). Kroemer et al. (1996) *Protein Eng.* 9(12):1135-1142. IL-7 appears to expand the T cell repertoire to allow more diverse targeting of tumor antigens. These and other activities of IL-7 have made the cytokine a potential candidate as a therapeutic protein to treat patients whose immune systems have been damaged by cancer chemotherapy, HIV infection, or other diseases, disorders, or chemical exposures. However, based on its immunostimulatory properties, therapeutically administered IL-7 is expected to induce an antibody response against itself. Therefore, there is a need in the art for improved versions of IL-7 that are less immunogenic, but that retain the property of stimulating the immune system.

In addition, the relatively high levels of IL-7 that can occur following exogenous administration of IL-7 can cause a profound and sustained reduction in the expression of IL-7 receptors. See, for example, Ghazawi et al. (2013) *Immunology and Cell Biology* 91:149-158. Thus, there is another need in the art for an IL-7-based therapy that results in sustained levels of an IL-7 agonist in a manner that avoids the reduction in expression of IL-7 receptors that is associated with relatively high levels the agonist.

Among other things, one or more embodiments of the present invention are therefore directed to forms of IL-7 that possess one or more of the following features as compared with IL-7: reduced immunogenicity; reduced or slowed elimination; activation of immune responses more localized to the tumor environment; and sustained and durable signaling through the JAK/STAT pathway, as well as compositions comprising the conjugates and related methods as described herein, which are believed to be new and completely unsuggested by the art.

SUMMARY

Accordingly, in one or more embodiments of the invention, a conjugate is provided, the conjugate comprising a residue of an IL-7 moiety covalently attached to a water-soluble polymer.

In one or more embodiments of the invention, a conjugate is provided, the conjugate comprising a residue of an IL-7 moiety covalently attached to a water-soluble polymer, wherein the residue of the IL-7 moiety is covalently attached to the water-soluble polymer via a releasable linkage.

In one or more embodiments of the invention, a conjugate is provided, the conjugate comprising a residue of an IL-7 moiety covalently attached to a water-soluble polymer, wherein the residue of the IL-7 moiety is covalently attached to the water-soluble polymer via a non-releasable linkage, preferably wherein the water-soluble polymer has a weight-average molecular weight of greater than 5,000 Daltons.

In one or more embodiments of the invention, a conjugate is provided, the conjugate comprising a residue of an IL-7 moiety covalently attached to a water-soluble polymer, wherein the IL-7 moiety is free of cysteine residues not involved with disulfide bonding.

In one or more embodiments of the invention, a conjugate is provided, the conjugate comprising a residue of an IL-7 moiety covalently attached to a water-soluble polymer, wherein the IL-7 moiety has an additional cysteine residue compared to human IL-7, and the water-soluble polymer is covalently attached to the additional cysteine residue.

In one or more embodiments of the invention, a conjugate is provided, the conjugate comprising a residue of an IL-7 moiety covalently attached to a branched water-soluble polymer.

In one or more embodiments of the invention, a conjugate is provided, the conjugate comprising a residue of an IL-7 moiety covalently attached to a water-soluble polymer, wherein an amine of the IL-7 moiety is covalently attached to the water-soluble polymer via a linkage other than an amide linkage.

In one or more embodiments of the invention, a conjugate is provided, the conjugate comprising a residue of an IL-7 moiety covalently attached to a water-soluble polymer, wherein an amine of the IL-7 moiety is covalently attached to the water-soluble polymer via an amine linkage.

In one or more embodiments of the invention, a composition is provided, the composition comprising a conjugate as described herein along with a pharmaceutically acceptable excipient.

In one or more embodiments of the invention, a method for delivering a conjugate is provided, the method comprising the step of subcutaneously administering to the patient a composition comprised of a conjugate of a residue of an IL-7 and a water-soluble polymer.

DETAILED DESCRIPTION

Figure 1:
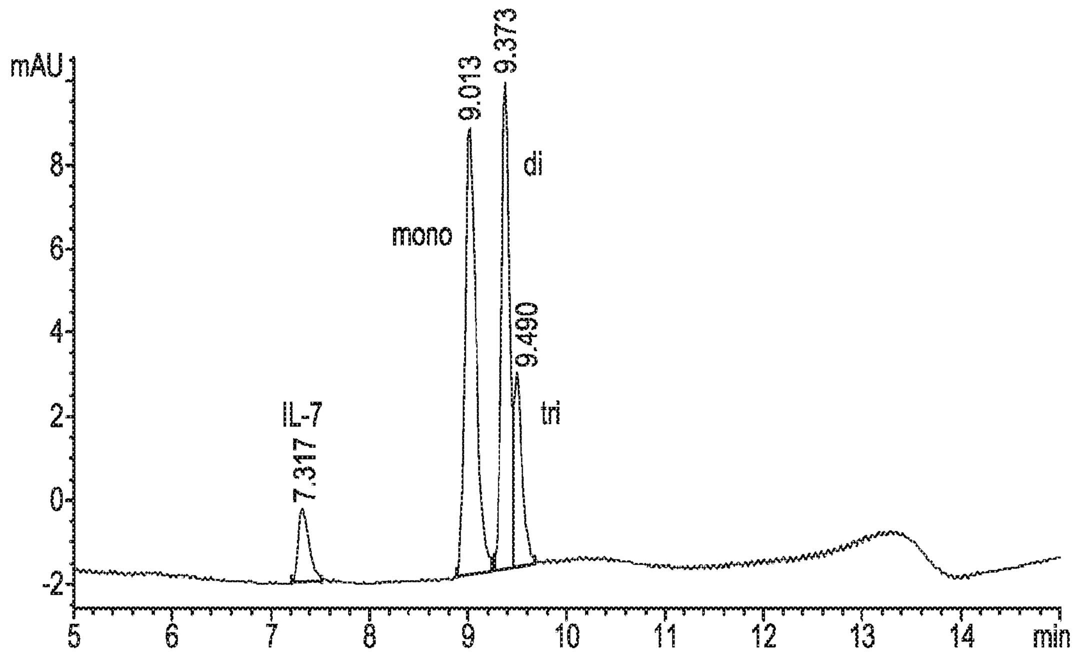
FIG. 1 is a plot of the RP-HPLC analysis of mPEG2-NHS, 20 kDa-IL-7 conjugate solution prepared as described in Example 1.

Before describing one or more embodiments of the present invention in detail, it is to be understood that this invention is not limited to the particular polymers, synthetic techniques, IL-7 moieties, and the like, as such may vary.

It must be noted that, as used in this specification and the intended claims, the singular forms "a," "an," and "the" include plural referents unless the context clearly dictates otherwise. Thus, for example, reference to "a polymer" includes a single polymer as well as two or more of the same or different polymers, reference to "an optional excipient" refers to a single optional excipient as well as two or more of the same or different optional excipients, and the like.

In describing and claiming one or more embodiments of the present invention, the following terminology will be used in accordance with the definitions described below.

"PEG," "polyethylene glycol" and "poly (ethylene glycol)" as used herein, are interchangeable and encompass any non-peptidic, water-soluble poly (ethylene oxide). Typically, PEGs for use in accordance with the Invention comprise the following structure "$-(OCH_2CH_2)_n$-" where (n) is 2 to 4000. As used herein, PEG also includes "$-CH_2CH_2-O(CH_2CH_2O)_n-CH_2CH_2-$" and "$-(OCH_2CH_2)_nO-$," depending upon whether or not the terminal oxygens have been displaced, e.g., during a synthetic transformation. Throughout the specification and claims, it should be remembered that the term "PEG" includes structures having various terminal or "end capping" groups and so forth. The term "PEG" also means a polymer that contains a majority, that is to say, greater than 50%, of $-OCH_2CH_2$-repeating subunits. With respect to specific forms, the PEG can take any number of a variety of molecular weights, as well as structures or geometries such as "branched," "linear," "forked," "multifunctional," and the like, to be described in greater detail below.

The terms "end-capped" and "terminally capped" are interchangeably used herein to refer to a terminal or end-point of a polymer having an end-capping moiety. Typically, although not necessarily, the end-capping moiety comprises a hydroxy or $C_{1-20}$ alkoxy group, more preferably a $C_{1-10}$ alkoxy group, and still more preferably a $C_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer [e.g., the end-capping moiety "methoxy" in $CH_3O(CH_2CH_2O)_n-$ and $CH_3(OCH_2CH_2)_n-$]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleoylphosphatidylcholine, dipalmitoylphosphatidylcholine, distearoylphosphatidylcholine, behenoylphosphatidylcholine, arachidoylphosphatidylcholine, and lecithin. The end-capping group may also include a targeting moiety, such that the polymer—as well as anything, e.g., an IL-7 moiety, attached thereto—can preferentially localize in an area of interest.

"Non-naturally occurring" with respect to a polymer as described herein, means a polymer that in its entirety is not found in nature. A non-naturally occurring polymer may, however, contain one or more monomers or segments of monomers that are naturally occurring, so long as the overall polymer structure is not found in nature.

The term "water soluble" as in a "water-soluble polymer" polymer is any polymer that is soluble in water at room temperature. Typically, a water-soluble polymer will transmit at least about 75%, more preferably at least about 95%, of light (e.g., of a wavelength of 600 nm) transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

Molecular weight in the context of a water-soluble polymer, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight or the use of light scattering techniques, ultracentrifugation, or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

The terms "active," "reactive" or "activated" when used in conjunction with a particular functional group, refer to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "spacer moiety," "linkage" and "linker" are used herein to refer to a bond or an atom or a collection of atoms optionally used to link interconnecting moieties such as a terminus of a polymeric reagent and an IL-7 moiety or an electrophile or nucleophile of an IL-7 moiety. The spacer moiety may be hydrolytically stable or may include a physiologically hydrolyzable or enzymatically degradable linkage. Unless the context clearly dictates otherwise, a spacer moiety optionally exists between any two elements of a compound (e.g., the provided conjugates comprising a residue of IL-7 moiety and water-soluble polymer can be attached directly or indirectly through a spacer moiety).

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 3-methylpentyl, and the like.

"Lower alkyl" refers to an alkyl group containing from 1 to 6 carbon atoms, and may be straight chain or branched, as exemplified by methyl, ethyl, n-butyl, i-butyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —OR group, wherein R is alkyl or substituted alkyl, preferably $C_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl, $C_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

An "organic radical" as used herein shall include alkyl, substituted alkyl, aryl, and substituted aryl.

"Electrophile" and "electrophilic group" refer to an ion or atom or collection of atoms, which may be ionic, having an electrophilic center, i.e., a center that is electron seeking, capable of reacting with a nucleophile.

"Nucleophile" and "nucleophilic group" refers to an ion or atom or collection of atoms that may be ionic having a nucleophilic center, i.e., a center that is seeking an electrophilic center or with an electrophile.

An "enzymatically degradable linkage" means a linkage that is subject to degradation by one or more enzymes.

A "hydrolyzable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides. A "releasable bond" is a covalent linkage that cleaves under physiological conditions at a rate that is clinically useful and includes, for example and without limitation, hydrolyzable bonds and enzymatically degradable linkage.

A "hydrolytically stable" linkage or bond refers to a chemical bond, typically a covalent bond, which is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Pharmaceutically acceptable excipient or carrier" refers to an excipient that may optionally be included in the compositions of the invention and that causes no significant adverse toxicological effects to the patient.

"Pharmacologically effective amount," "physiologically effective amount," and "therapeutically effective amount" are used interchangeably herein to mean the amount of a polymer-(IL-7) moiety conjugate that is needed to provide a desired level of the conjugate (or corresponding unconjugated IL-7 moiety) in the bloodstream or in the target tissue. The precise amount will depend upon numerous factors, e.g., the particular IL-7 moiety, the components and physical characteristics of the therapeutic composition, intended patient population, individual patient considerations, and the like, and can readily be determined by one skilled in the art, based upon the information provided herein.

"Multi-functional" means a polymer having three or more functional groups contained therein, where the functional groups may be the same or different. Multi-functional polymeric reagents of the invention will typically contain from about 3-100 functional groups, and can contain, for example, a number satisfying one or more of the following ranges: from 3-50 functional groups; from 3-25 functional groups; from 3-15 functional groups; from 3 to 10 functional groups. For example, the number of functional groups can be selected from the group consisting of 3, 4, 5, 6, 7, 8, 9 and 10 functional groups within the polymer backbone.

The term "IL-7 moiety," as used herein, refers to a peptide or protein moiety having human IL-7 activity. The IL-7 moiety will also have at least one electrophilic group or nucleophilic group suitable for reaction with a polymeric reagent. In addition, the term "IL-7 moiety" encompasses both the IL-7 moiety prior to conjugation as well as the IL-7 moiety residue following conjugation. As will be explained in further detail below, one of ordinary skill in the art can determine whether any given moiety has IL-7 activity. Proteins comprising an amino acid sequence corresponding to any one of SEQ ID NOs: 1 through 8 is an IL-7 moiety, as well as any protein or polypeptide substantially homologous thereto. As used herein, the term "IL-7 moiety" includes such peptides and proteins modified deliberately, as for example, by site directed mutagenesis or accidentally through mutations. These terms also include analogs having from 1 to 6 additional glycosylation sites, analogs having at least one additional amino acid at the carboxy terminal end of the peptide or protein wherein the additional amino acid(s) includes at least one glycosylation site, and analogs having an amino acid sequence which includes at least one glycosylation site. The term includes naturally, recombinantly and synthetically produced moieties.

The term "substantially homologous" means that a particular subject sequence, for example, a mutant sequence, varies from a reference sequence by one or more substitutions, deletions, or additions, the net effect of which does not result in an adverse functional dissimilarity between the reference and subject sequences. For purposes of the present invention, sequences having greater than 95 percent homology, equivalent biological activity (although not necessarily equivalent strength of biological activity), and equivalent expression characteristics are considered substantially homologous. For purposes of determining homology, truncation of the mature sequence should be disregarded. Exemplary IL-7 moieties for use herein include those sequences that are substantially homologous SEQ ID NO: 1.

The term "fragment" means any protein or polypeptide having the amino acid sequence of a portion or fragment of an IL-7 moiety, and which has the biological activity of IL-7. Fragments include proteins or polypeptides produced by proteolytic degradation of an IL-7 moiety as well as proteins or polypeptides produced by chemical synthesis by methods routine in the art.

The term "patient," refers to a living organism suffering from or prone to a condition that can be prevented or treated by administration of an active agent (e.g., conjugate), and includes both humans and animals.

"Optional" or "optionally" means that the subsequently described circumstance may or may not occur, so that the description includes instances where the circumstance occurs and instances where it does not.

"Substantially" means nearly totally or completely, for instance, satisfying one or more of the following: greater than 50%, 51% or greater, 75% or greater, 80% or greater, 90% or greater, and 95% or greater of the condition.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

Turning to one or more embodiments of the invention, a conjugate is provided, the conjugate comprising a residue of an IL-7 moiety covalently attached (either directly or through a spacer moiety) to a water-soluble polymer. The conjugates of the invention will have one or more of the following features.

The IL-7 Moiety

As previously stated, the conjugate comprises a residue of an IL-7 moiety covalently attached, either directly or through a spacer moiety, to a water-soluble polymer. As used herein, the term "IL-7 moiety" shall refer to the IL-7 moiety prior to conjugation as well as to the IL-7 moiety following attachment to a nonpeptidic, water-soluble polymer. It will be understood, however, that when the original IL-7 moiety is attached to a non-peptidic, water-soluble polymer, the IL-7 moiety is slightly altered due to the presence of one or more covalent bonds associated with linkage to the polymer (s). Often, this slightly altered form of the IL-7 moiety attached to another molecule is referred to as a "residue" of the IL-7 moiety.

The IL-7 moiety can be derived from non-recombinant methods and from recombinant methods and the invention is not limited in this regard. In addition, the IL-7 moiety can be derived from human sources, animal sources (including insects), fungi sources (including yeasts), and plant sources.

The IL-7 moiety can be obtained according to the procedures described by Namen et al. (1998) *J Exp. Med.* 167: 988-1002 et al.

The IL-7 moiety can be derived from recombinant methods. See, for example, Ouellette et al. (2003) *Protein Expression and Purification* 30:156-166.

The IL-7 moiety can be purchased commercially from, for example, eBioscience, Inc., San Diego, CA.

The IL-7 moiety can be expressed in bacterial [e.g., *E. coli*, see, for example, Fischer et al. (1995) *Biotechnol. Appl. Biotechnol.* 21(3):295-311], mammalian [see, for example, Kronman et al. (1992) *Gene* 121:295-304], yeast [e.g., *Pichia pastoris*, see, for example, Morel et al. (1997) *Biochem. I* 328(1):121-129], and plant [see, for example, Mor et al. (2001) *Biotechnol. Bioeng.* 75(3):259-266] expression systems. The expression can occur via exogenous expression (when the host cell naturally contains the desired genetic coding) or via endogenous expression.

Although recombinant-based methods for preparing proteins can differ, recombinant methods typically involve constructing the nucleic acid encoding the desired polypeptide or fragment, cloning the nucleic acid into an expression vector, transforming a host cell (e.g., plant, bacteria, yeast, transgenic animal cell, or mammalian cell such as Chinese hamster ovary cell or baby hamster kidney cell), and expressing the nucleic acid to produce the desired polypeptide or fragment. Methods for producing and expressing recombinant polypeptides in vitro and in prokaryotic and eukaryotic host cells are known to those of ordinary skill in the art.

To facilitate identification and purification of the recombinant polypeptide, nucleic acid sequences that encode for an epitope tag or other affinity binding sequence can be inserted or added in-frame with the coding sequence, thereby producing a fusion protein comprised of the desired polypeptide and a polypeptide suited for binding. Fusion proteins can be identified and purified by first running a mixture containing the fusion protein through an affinity column bearing binding moieties (e.g., antibodies) directed against the epitope tag or other binding sequence in the fusion proteins, thereby binding the fusion protein within the column. Thereafter, the fusion protein can be recovered by washing the column with the appropriate solution (e.g., acid) to release the bound fusion protein. The recombinant polypeptide can also be purified by lysing the host cells, separating the polypeptide, e.g., by ion-exchange chromatography, affinity binding approaches, hydrophobic interaction approaches, and thereafter identify by MALDI or western blot, and collecting the polypeptide. These and other methods for identifying and purifying recombinant polypeptides are known to those of ordinary skill in the art. In one or more embodiments of the invention, however, the IL-7 moiety is not in the form of a fusion protein.

Depending on the system used to express proteins having IL-7 activity, the IL-7 moiety can be unglycosylated or glycosylated and either may be used. That is, the IL-7 moiety can be unglycosylated or the IL-7 moiety can be glycosylated. In one or more embodiments of the invention, the IL-7 moiety is unglycosylated. In those embodiments in which the IL-7 moiety is glycosylated, conjugation can optionally occur on the carbohydrate (in the manner described in, for example, U.S. Pat. No. 7,956,032).

The IL-7 moiety can advantageously be modified to include and/or substitute one or more amino acid residues such as, for example, lysine, cysteine and/or arginine, in order to provide facile attachment of the polymer to an atom within the side chain of the amino acid. An example of substitution of an IL-7 moiety is described in U.S. Pat. No. 6,177,079. In addition, the IL-7 moiety can be modified to include a non-naturally occurring amino acid residue. Techniques for adding amino acid residues and non-naturally occurring amino acid residues are well known to those of ordinary skill in the art. Reference is made to J. March, Advanced Organic Chemistry: Reactions Mechanisms and Structure, 4th Ed. (New York: Wiley-Interscience, 1992).

In addition, the IL-7 moiety can advantageously be modified to include attachment of a functional group (other than through addition of a functional group-containing amino acid residue). For example, the IL-7 moiety can be modified to include a thiol group. In addition, the IL-7 moiety can be modified to include an N-terminal alpha carbon. In addition, the IL-7 moiety can be modified to include one or more carbohydrate moieties. In addition, the IL-7 moiety can be modified to include an aldehyde group. In addition, the IL-7 moiety can be modified to include a ketone group. In some embodiments of the invention, it is preferred that the IL-7 moiety is not modified to include one or more of a thiol group, an N-terminal alpha carbon, carbohydrate, aldehyde group and ketone group.

Exemplary IL-7 moieties are described herein, in the literature, and in, for example, U.S. Pat. No. 7,589,179, Wong et al. (2013) *OncoImmunology* 2(11), e26442:1-3, Romano et al. (1998) *Protein Engineering* 11(1):31-40, and Vudattu et al. (2009) *Genes and Immunity* 10:132-140. Preferred IL-7 moieties include those having an amino acid sequence comprising sequences selected from the group consisting of SEQ ID NOs: 1 through 8, and sequences substantially homologous thereto. A preferred IL-7 moiety has the amino acid sequence corresponding to SEQ ID NO: 1.

In some instances, the IL-7 moiety will be in a "monomer" form, wherein a single expression of the corresponding peptide is organized into a discrete unit. In other instances, the IL-7 moiety will be in the form of a "dimer" (e.g., a dimer of recombinant IL-7) wherein two monomer forms of the protein are associated to each other.

Truncated versions, hybrid variants, and peptide mimetics of any of the foregoing sequences can also serve as the IL-7 moiety. Biologically active fragments, deletion variants, substitution variants or addition variants of any of the foregoing that maintain at least some degree of IL-7 activity can also serve as an IL-7 moiety.

For any given peptide or protein moiety, it is possible to determine whether that moiety has IL-7 activity. Various methods for determining in vitro IL-7 activity are described in the art. For example, the bioactivity of any proposed IL-7 moiety and conjugate formed therefrom can be evaluated using the IL-7-dependent murine pro-B cell line 2E8, wherein cells from this line are exposed to the test article of interest at a range of concentrations for a defined period of time and the extent of phosphorylation of the signaling protein STATS is used as a quantitative measure of bioactivity. In such a test, test articles exhibiting at least one of the following qualities are understood as having IL-7 activity: (a) a level of STATS phosphorylation at least 10% of that elicited by a saturating dose of human, native IL-7; and (b) an EC50 that is less than 1000-fold higher than the EC50 of human, native IL-7. When the test article is a polymer conjugate of the invention, it is preferred that the conjugate will have a level of STATS phosphorylation at least 50% of that elicited by a saturating dose of human, native IL-7 and/or an EC50 that is less than 10-fold higher than the EC50 of human, native IL-7. It is understood that a polymer conjugate may exhibit a minimal amount of IL-7 bioactivity, but still be understood as a conjugate within the scope of the invention due to the release of one or more water-soluble polymers (wherein a "downstream" version of the conjugate, e.g., a version lacking one or more of the water-soluble polymers relative to the version administered to the patient, does exhibit at least one of the following qualities: (a) a level of STATS phosphorylation at least 10% of that elicited by a saturating dose of human, native IL-7; and (b) an EC50 that is less than 1000-fold higher than the EC50 of human, native IL-7).

Other methodologies known in the art can also be used to assess IL-7 function, including electrometry, spectrophotometry, chromatography, and radiometric methodologies.

Assays for use in connection with measuring the activity of an IL-7 moiety can also be used to measure the activity of conjugates described herein. Due to a given conjugate's properties (e.g., incorporation of a releasable linkage, ability to withstand metabolism, increased half-life, selective binding properties, and so forth), however, the conjugate need not necessarily exhibit the same activity as an IL-7 moiety defined herein.

The Water-Soluble Polymer

As previously discussed, each conjugate comprises an IL-7 moiety attached to a water-soluble polymer. With respect to the water-soluble polymer, the water-soluble polymer is non-peptidic, non-toxic, non-naturally occurring and biocompatible. With respect to biocompatibility, a substance is considered biocompatible if the beneficial effects associated with use of the substance alone or with another substance (e.g., an active agent such as an IL-7 moiety) in connection with living tissues (e.g., administration to a patient) outweighs any deleterious effects as evaluated by a clinician, e.g., a physician. With respect to non-immunogenicity, a substance is considered non-immunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the non-peptidic water-soluble polymer is biocompatible and non-immunogenic.

Further, the polymer is typically characterized as having from 2 to about 300 termini. Examples of such polymers include, but are not limited to, poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines ("POZ") (which are described in WO 2008/106186), poly(N-acryloylmorpholine), and combinations of any of the foregoing.

The water-soluble polymer is not limited to a particular structure and can be linear (e.g., an end capped, e.g., alkoxy PEG or a bifunctional PEG), branched or multi-armed (e.g., forked PEG or PEG attached to a polyol core), a dendritic (or star) architecture, each with or without one or more degradable linkages. Moreover, the internal structure of the water-soluble polymer can be organized in any number of different repeat patterns and can be selected from the group consisting of homopolymer, alternating copolymer, random copolymer, block copolymer, alternating tripolymer, random tripolymer, and block tripolymer.

Typically, activated PEG and other activated water-soluble polymers (i.e., polymeric reagents) are activated with a suitable activating group appropriate for coupling to a desired site on the IL-7 moiety. Thus, a polymeric reagent will possess a reactive group for reaction with the IL-7 moiety. Representative polymeric reagents and methods for conjugating these polymers to an active moiety are known in the art and further described in Zalipsky, S., et al., "*Use of Functionalized Poly(Ethylene Glycols) for Modification of Polypeptides*" in Polyethylene Glycol Chemistry: Biotechnical and Biomedical Applications, J. M. Harris, Plenus Press, New York (1992), and in Zalipsky (1995)*Advanced Drug Reviews* 16:157-182. Exemplary activating groups suitable for coupling to an IL-7 moiety include hydroxyl, maleimide, ester, acetal, ketal, amine, carboxyl, aldehyde, aldehyde hydrate, ketone, vinyl ketone, thione, thiol, vinyl sulfone, hydrazine, among others.

Typically, the weight-average molecular weight of the water-soluble polymer in the conjugate is from about 100 Daltons to about 150,000 Daltons. Exemplary ranges, however, include weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons. For any given water-soluble polymer, PEGs having a molecular weight in one or more of these ranges are preferred.

Exemplary weight-average molecular weights for the water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total molecular weight of any of the foregoing can also be used. In one or more embodiments, the conjugate will not have any PEG moieties attached, either directly or indirectly, with a PEG having a weight average molecular weight of less than about 6,000 Daltons.

When used as the polymer, PEGs will typically comprise a number of $(OCH_2CH_2)$ monomers [or $(CH_2CH_2O)$ monomers, depending on how the PEG is defined]. As used throughout the description, the number of repeating units is identified by the subscript "n" in "$(OCH_2CH_2)_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

One particularly preferred polymer for use in the invention is an end-capped polymer, that is, a polymer having at least one terminus capped with a relatively inert group, such as a lower $C_{1-6}$ alkoxy group, although a hydroxyl group can also be used. When the polymer is PEG, for example, it is preferred to use a methoxy-PEG (commonly referred to as mPEG), which is a linear form of PEG wherein one terminus of the polymer is a methoxy ($—OCH_3$) group, while the other terminus is a hydroxyl or other functional group that can be optionally chemically modified.

In one form useful in one or more embodiments of the present invention, free or unbound PEG is a linear polymer terminated at each end with hydroxyl groups:

$$HO—CH_2CH_2O—(CH_2CH_2O)_n—CH_2CH_2—OH,$$

wherein (n) typically ranges from zero to about 4,000.

The above polymer, alpha-, omega-dihydroxylpoly(ethylene glycol), can be represented in brief form as HO-PEG-OH where it is understood that the -PEG- symbol can represent the following structural unit:

$$—CH_2CH_2O—(CH_2CH_2O)_n—CH_2CH_2—,$$

wherein (n) is as defined as above.

Another type of PEG useful in one or more embodiments of the present invention is methoxy-PEG-OH, or mPEG in brief, in which one terminus is the relatively inert methoxy group, while the other terminus is a hydroxyl group. The structure of mPEG is given below.

$$CH_3O—CH_2CH_2O—(CH_2CH_2O)_n—CH_2CH_2—OH$$

wherein (n) is as described above.

Multi-armed or branched PEG molecules, such as those described in U.S. Pat. No. 5,932,462, can also be used as the PEG polymer. For example, PEG can have the structure:

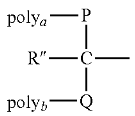

wherein:

- $poly_a$ and $poly_b$ are PEG backbones (either the same or different), such as methoxy poly(ethylene glycol);
- R" is a nonreactive moiety, such as H, methyl or a PEG backbone; and
- P and Q are nonreactive linkages. In a preferred embodiment, the branched PEG polymer is methoxy poly (ethylene glycol) disubstituted lysine. Depending on the specific IL-7 moiety used, the reactive ester functional group of the disubstituted lysine may be further modified to form a functional group suitable for reaction with the target group within the IL-7 moiety.

In addition, the PEG can comprise a forked PEG. An example of a forked PEG is represented by the following structure:

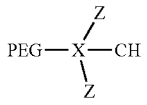

wherein: X is a spacer moiety of one or more atoms and each Z is an activated terminal group linked to CH by a chain of atoms of defined length. International Patent Application Publication WO 99/45964 discloses various forked PEG structures capable of use in one or more embodiments of the present invention. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, the polymer can also be prepared with one or more weak or degradable linkages in the polymer, including any of the above-described polymers. For example, PEG can be prepared with ester linkages in the polymer that are subject to hydrolysis. As shown below, this hydrolysis results in cleavage of the polymer into fragments of lower molecular weight:

$$\text{-PEG-}CO_2\text{—PEG-}+H_2O \longrightarrow \text{-PEG-}CO_2H+\text{HO-PEG-}$$

Other hydrolytically degradable linkages, useful as a degradable linkage within a polymer backbone and/or as a degradable linkage to an IL-7 moiety, include: carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; orthoester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

Such optional features of the conjugate, i.e., the introduction of one or more degradable linkages into the polymer chain or to the IL-7 moiety, may provide for additional control over the final desired pharmacological properties of the conjugate upon administration. For example, a large and relatively inert conjugate (i.e., having one or more high molecular weight PEG chains attached thereto, for example, one or more PEG chains having a molecular weight greater than about 10,000, wherein the conjugate possesses essentially no bioactivity) may be administered, which is hydrolyzed to generate a bioactive conjugate possessing a portion of the original PEG chain. In this way, the properties of the conjugate can be more effectively tailored to balance the bioactivity of the conjugate over time.

The water-soluble polymer associated with the conjugate can also be “releasable.” That is, the water-soluble polymer releases (either through hydrolysis, enzymatic processes, catalytic processes or otherwise), thereby resulting in the unconjugated IL-7 moiety. In some instances, releasable polymers detach from the IL-7 moiety in vivo without leaving any fragment of the water-soluble polymer. In other instances, releasable polymers detach from the IL-7 moiety in vivo leaving a relatively small fragment (e.g., a succinate tag) from the water-soluble polymer. An exemplary cleavable polymer includes one that attaches to the IL-7 moiety via a carbonate linkage.

Those of ordinary skill in the art will recognize that the foregoing discussion concerning non-peptidic and water-soluble polymer is by no means exhaustive and is merely illustrative, and that all polymeric materials having the qualities described above are contemplated. As used herein, the term “polymeric reagent” generally refers to an entire molecule, which can comprise a water-soluble polymer segment and a functional group.

As described above, a conjugate of the invention comprises a water-soluble polymer covalently attached to an IL-7 moiety. Typically, for any given conjugate, there will be one to three water-soluble polymers covalently attached to one or more moieties having IL-7 activity. In some instances, however, the conjugate may have 1, 2, 3, 4, 5, 6, 7, 8 or more water-soluble polymers individually attached to an IL-7 moiety. Any given water-soluble polymer may be covalently attached to either an amino acid of the IL-7 moiety, or, when the IL-7 moiety is (for example) a glycoprotein, to a carbohydrate of the IL-7 moiety. Attachment to a carbohydrate may be carried out, e.g., using metabolic functionalization employing sialic acid-azide chemistry [Luchansky et al. (2004) *Biochemistry* 43(38):12358-12366] or other suitable approaches such as the use of glycidol to facilitate the introduction of aldehyde groups [Heldt et al. (2007) *European Journal of Organic Chemistry* 32:5429-5433].

The particular linkage within the moiety having IL-7 activity and the polymer depends on a number of factors. Such factors include, for example, the particular linkage chemistry employed, the particular IL-7 moiety, the available functional groups within the IL-7 moiety (either for attachment to a polymer or conversion to a suitable attachment site), the presence of additional reactive functional groups within the IL-7 moiety, and the like.

The conjugates of the invention can be, although not necessarily, prodrugs, meaning that the linkage between the polymer and the IL-7 moiety is hydrolytically releasable to allow release of the parent moiety. Exemplary releasable linkages include carboxylate ester, phosphate ester, thiol ester, anhydrides, acetals, ketals, acyloxyalkyl ether, imines, orthoesters, peptides and oligonucleotides. Such linkages can be readily prepared by appropriate modification of either the IL-7 moiety (e.g., the carboxyl group C terminus of the protein, or a side chain hydroxyl group of an amino acid such as serine or threonine contained within the protein, or a similar functionality within the carbohydrate) and/or the polymeric reagent using coupling methods commonly employed in the art. Most preferred, however, are hydrolyzable linkages that are readily formed by reaction of a suitably activated polymer with a non-modified functional group contained within the moiety having IL-7 activity.

Alternatively, a hydrolytically stable linkage, such as an amide, urethane (also known as carbamate), amine, thioether (also known as sulfide), or urea (also known as carbamide) linkage can also be employed as the linkage for coupling the IL-7 moiety. Again, a preferred hydrolytically stable linkage is an amide. In one approach, a water-soluble polymer bearing an activated ester can be reacted with an amine group on the IL-7 moiety to thereby result in an amide linkage.

The conjugates (as opposed to an unconjugated IL-7 moiety) may or may not possess a measurable degree of IL-7 activity. That is to say, a polymer-IL-7 moiety conjugate in accordance with the invention will possesses anywhere from about 0.1% to about 100% of the bioactivity of the unmodified parent IL-7 moiety. In some instances, the polymer-IL-7 moiety conjugates may have greater than 100% bioactivity of the unmodified parent IL-7 moiety. Preferably, conjugates possessing little or no IL-7 activity contain a hydrolyzable linkage connecting the polymer to the moiety, so that regardless of the lack (or relatively lack) of activity in the conjugate, the active parent molecule (or a derivative thereof) is released upon aqueous-induced cleavage of the hydrolyzable linkage. Such activity may be determined using a suitable in-vivo or in-vitro model, depending upon the known activity of the particular moiety having IL-7 activity employed.

For conjugates possessing a hydrolytically stable linkage that couples the moiety having IL-7 activity to the polymer, the conjugate will typically possess a measurable degree of bioactivity. For instance, such conjugates are typically characterized as having a bioactivity satisfying one or more of the following percentages relative to that of the unconjugated IL-7 moiety: at least about 2%, at least about 5%, at least about 10%, at least about 15%, at least about 25%, at least about 30%, at least about 40%, at least about 50%, at least about 60%, at least about 80%, at least about 85%, at least about 90%, at least about 95%, at least about 97%, at least about 100%, and more than 105% (when measured in a suitable model, such as those well known in the art). Preferably, conjugates having a hydrolytically stable linkage (e.g., an amide linkage) will possess at least some degree of the bioactivity of the unmodified parent moiety having IL-7 activity.

Exemplary conjugates in accordance with the invention will now be described. Typically, such an IL-7 moiety is expected to share (at least in part) a similar amino acid sequence as the sequence provided in at least one of SEQ ID NOs: 1 through 7. Thus, while reference will be made to specific locations or atoms within SEQ ID NOs: 1 through 7, such a reference is for convenience only and one having ordinary skill in the art will be able to readily determine the corresponding location or atom in other moieties having IL-7 activity. In particular, the description provided herein for native human IL-7 is often applicable to fragments, deletion variants, substitution variants or addition variants of any of the foregoing.

Amino groups on IL-7 moieties provide a point of attachment between the IL-7 moiety and the water-soluble polymer. Using the amino acid sequence provided in SEQ ID NOs: 1 through 7, it is evident that there are several lysine residues in each having an ε-amino acid that may be available for conjugation. Further, the N-terminal amine of any protein can also serve as a point of attachment.

There are a number of examples of suitable polymeric reagents useful for forming covalent linkages with available amines of an IL-7 moiety. Specific examples, along with the corresponding conjugate, are provided in Table 1, below. In the table, the variable (n) represents the number of repeating monomeric units and "—NH—(IL-7)" represents the residue of the IL-7 moiety following conjugation to the polymeric reagent. While each polymeric portion [e.g., $(OCH_2CH_2)_n$ or $(CH_2CH_2O)_n$] presented in Table 1 terminates in a "$CH_3$" group, other groups (such as H and benzyl) can be substituted therefor.

TABLE 1

| Amine-Selective Polymeric Reagents and the IL-7 Moiety Conjugate Formed Therefrom |
| --- |
| Polymeric Reagent |
| 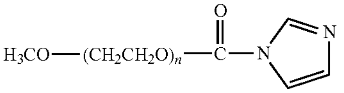 |
| mPEG-Oxycarbonylimidazole Reagents |
| 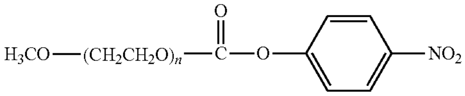 |
| mPEG Nitrophenyl Reagents |
| 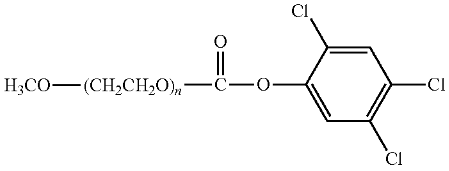 |
| mPEG-Trichlorophenyl Carbonate Reagents |
| 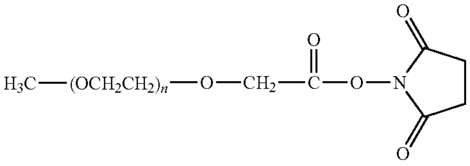 |
| mPEG-Succinimidyl Reagents |
| 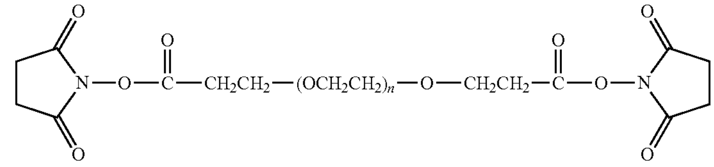 |
| Homobifunctional PEG-Succinimidyl Reagents |
| 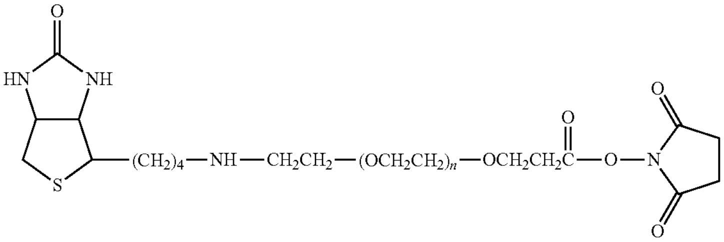 |
| Heterobifunctional PEG-Succinimidyl Reagents |
| 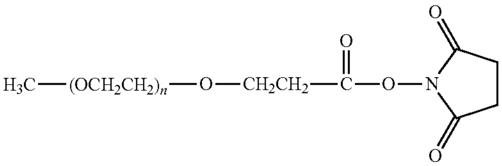 |
| mPEG-Succinimidyl Reagents |

TABLE 1-continued
Amine-Selective Polymeric Reagents and the IL-7 Moiety Conjugate Formed Therefrom
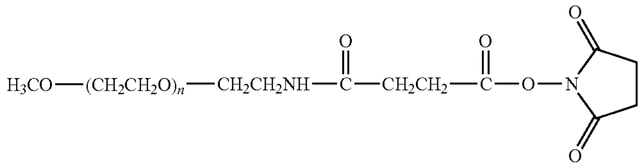
mPEG-Succinimdyl Reagents
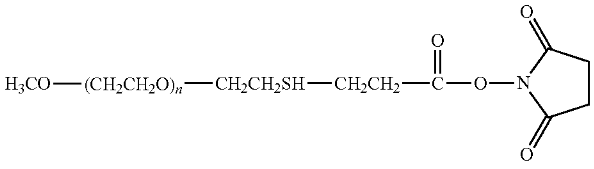
mPEG Succinimidyl Reagents
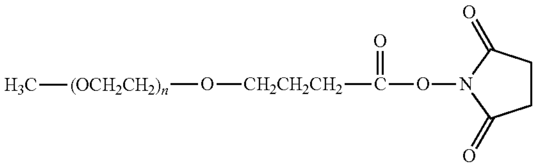
mPEG-Succinimidyl Reagents
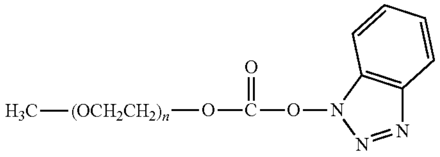
mPEG-Benzotriazole Carbonate Reagents
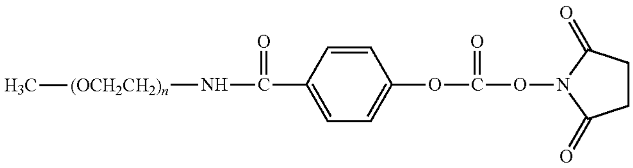
mPEG-Succinimidyl Reagents
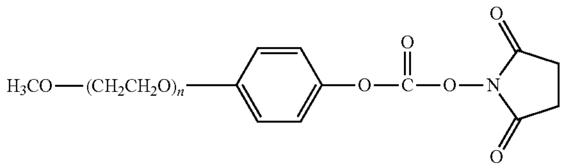
mPEG-Succinimidyl Reagents
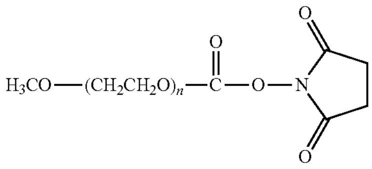
mPEG Succinimidyl Reagents TABLE 1-continued
Amine-Selective Polymeric Reagents and the IL-7 Moiety Conjugate Formed Therefrom
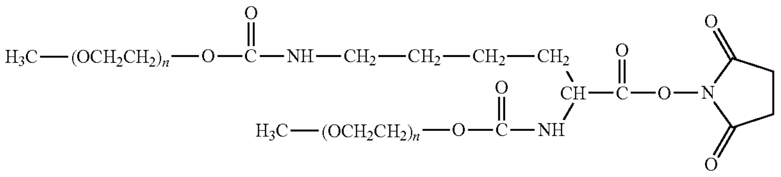
Branched mPEG2-N-Hydroxysuccinimide Reagents
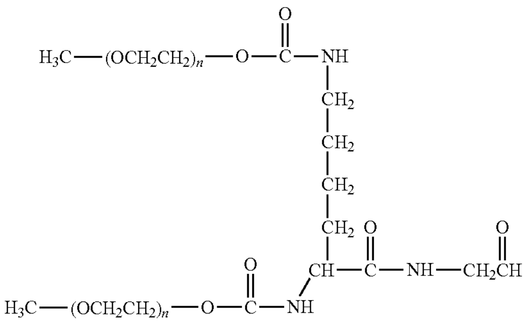
Branched mPEG2-Aldehyde Reagents
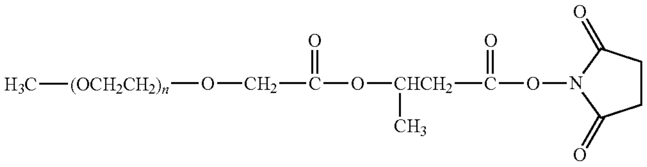
mPEG-Succinimidyl Reagents
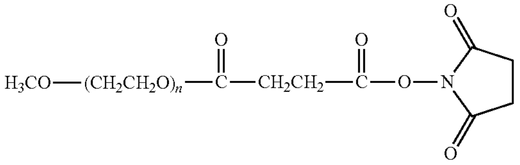
mPEG-Succinimidyl Reagents
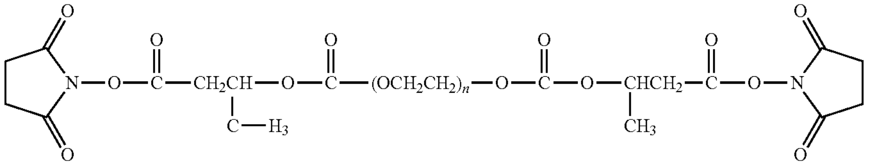
Homobifunctional PEG-Succinimidyl Reagents
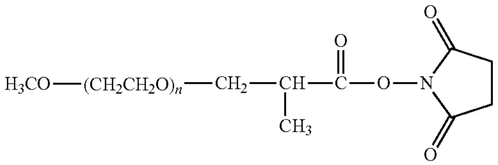
mPEG-Succinimidyl Reagents TABLE 1-continued

| Amine-Selective Polymeric Reagents and the IL-7 Moiety Conjugate Formed Therefrom |
| --- |
| 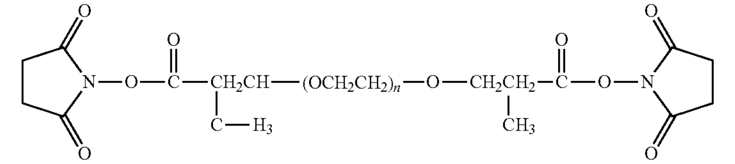<br>Homobifunctional PEG-Succinimidyl Propionate Reagents |
| 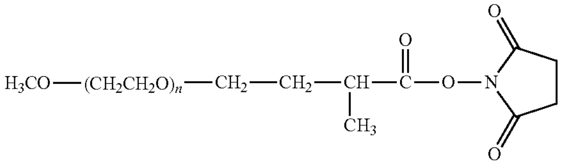<br>mPEG-Succinimidyl Reagents |
| 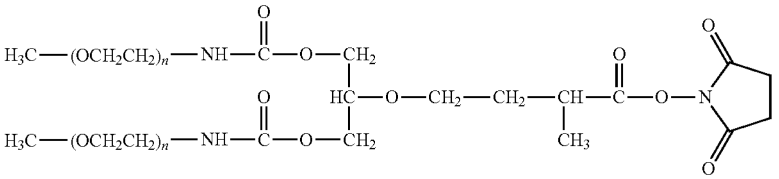<br>Branched mPEG2-N-Hydroxysuccinimide Reagents |
| 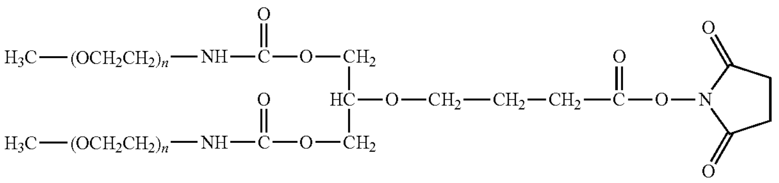<br>Branched mPEG2-N-Hydroxysuccinimide Reagents |
| 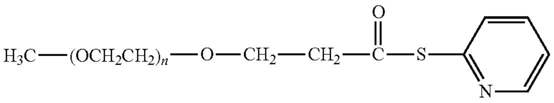<br>mPEG-Thioester Reagents |
| 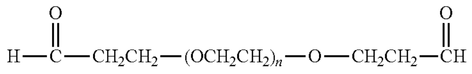<br>Homobifunctional PEG Propionaldehyde Reagents |
| 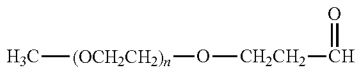<br>mPEG Propionaldehyde Reagents |
| 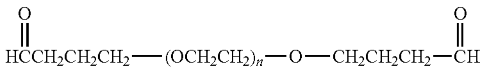<br>Homobifunctional PEG Butyraldehyde Reagents |

TABLE 1-continued

Amine-Selective Polymeric Reagents and the IL-7 Moiety Conjugate Formed Therefrom

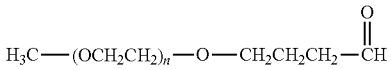

mPEG Butryaldehyde Reagents

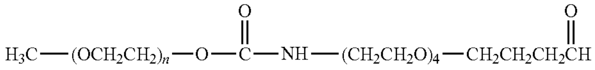

mPEG Butryaldehyde Reagents

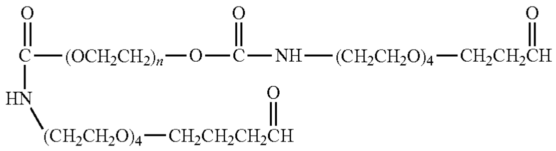

Homobifunctional PEG Butryaldehyde Reagents

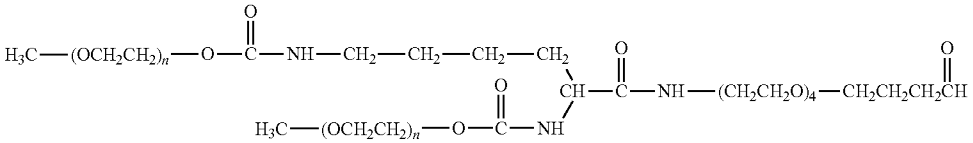

Branched mPEG2 Butyraldehyde Reagents

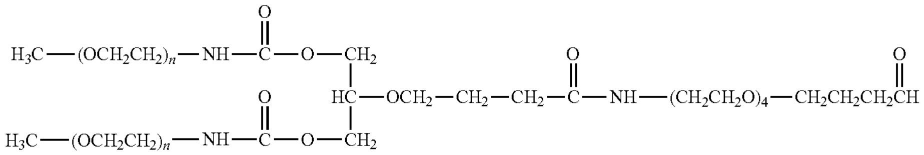

Branched mPEG2 Butyraldehyde Reagents

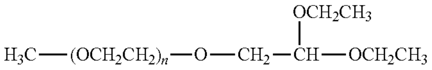

mPEG Acetal Reagents

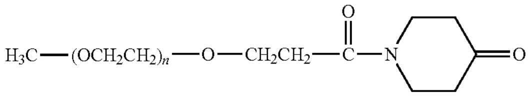

mPEG Piperidone Reagents

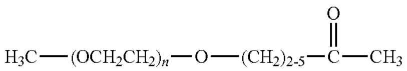

mPEG Methylketone Reagents

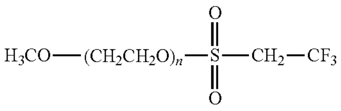

mPEG Tresylate Reagents

TABLE 1-continued

Amine-Selective Polymeric Reagents and the IL-7 Moiety Conjugate Formed Therefrom

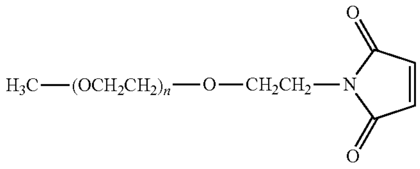

mPEG Maleimide Reagents
(under certain reaction conditions such as pH > 8)

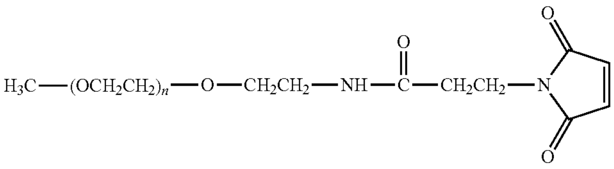

mPEG Maleimide Reagents
(under certain reaction conditions such as pH > 8)

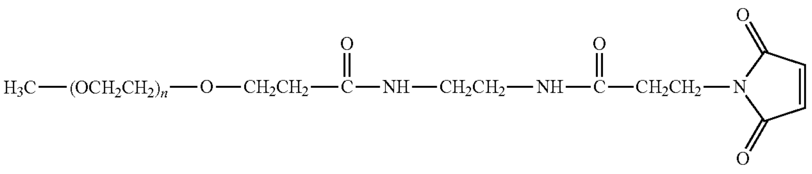

mPEG Maleimide Reagents
(under certain reaction conditions such as pH > 8)

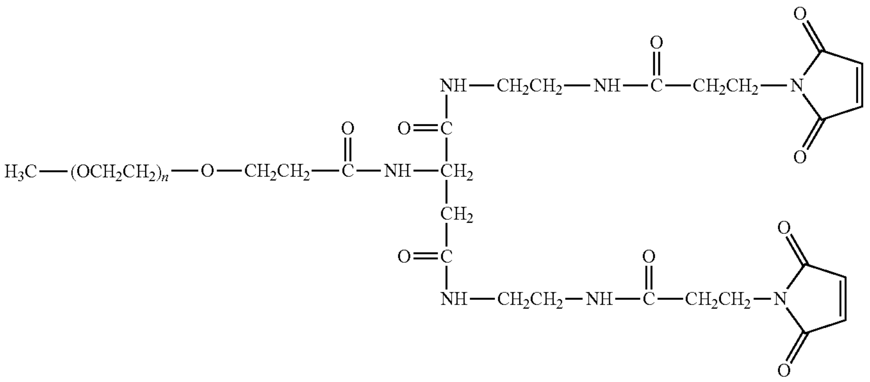

mPEG Forked Maleimide Reagents
(under certain reaction conditions such as pH > 8)

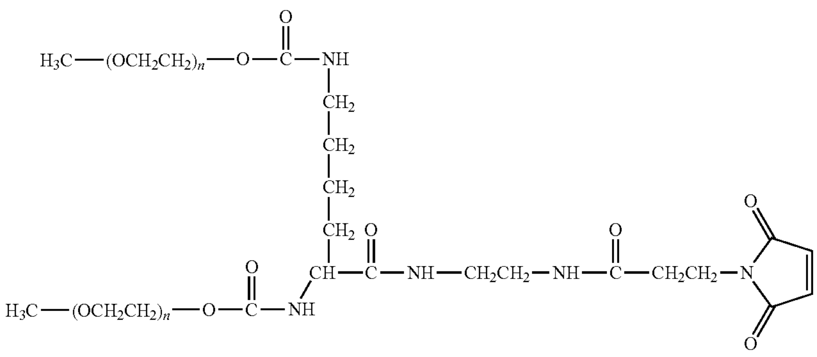

branched mPEG2 Maleimide Reagents
(under certain reaction conditions such as pH > 8)

TABLE 1-continued
| Amine-Selective Polymeric Reagents and the IL-7 Moiety Conjugate Formed Therefrom |
|---|
| 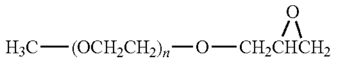<br>mPEG Epoxide Reagents<br>(under certain reaction conditions such as pH > 8) |
| 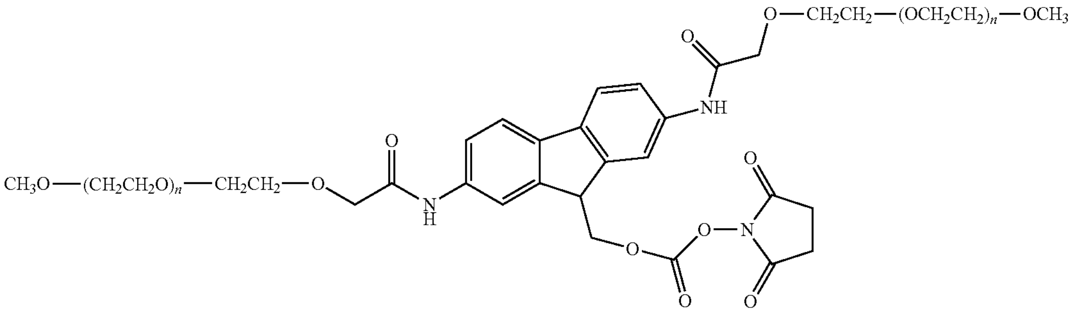<br>Branched mPEG Derivative |
| 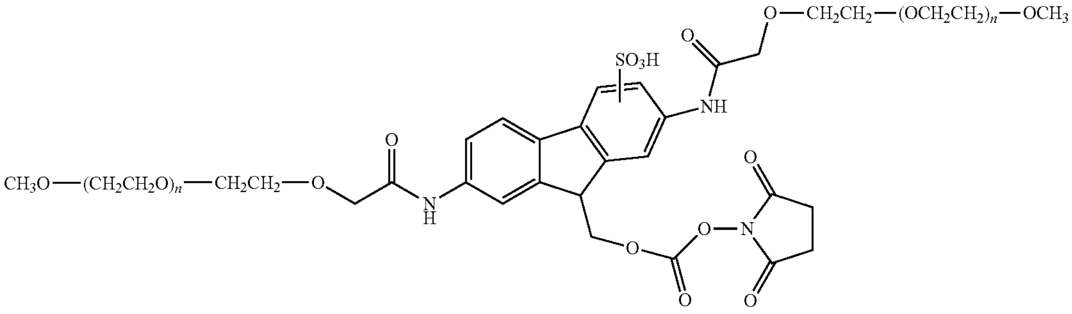<br>Branched mPEG Derivative |
| 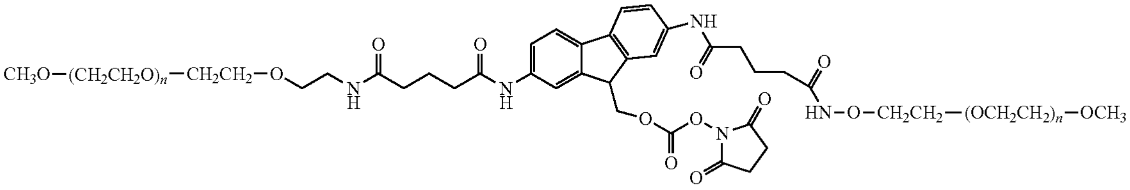<br>Branched mPEG Derivative |
| 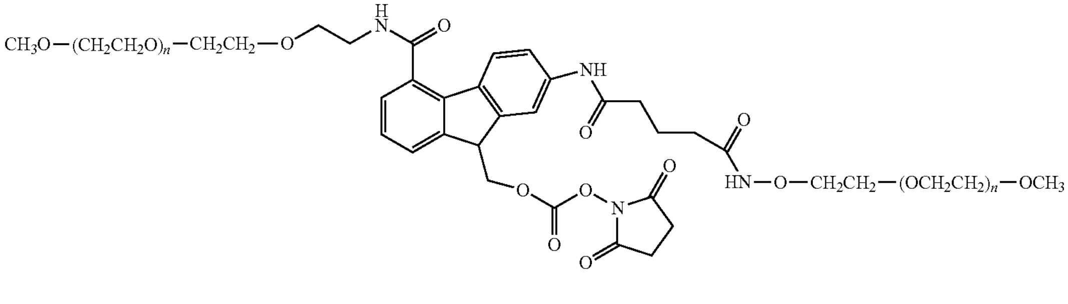<br>Branched mPEG Derivative |

TABLE 1-continued

| Amine-Selective Polymeric Reagents and the IL-7 Moiety Conjugate Formed Therefrom |
|---|
| 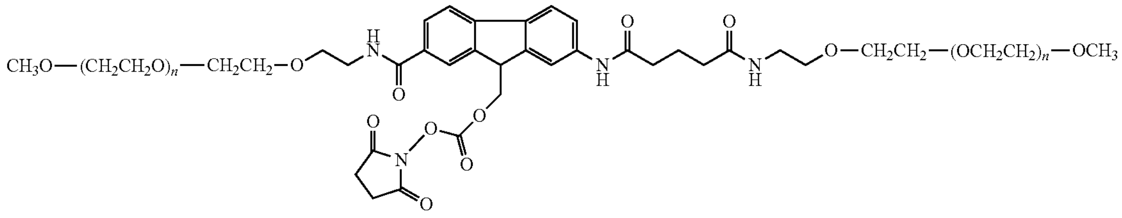<br>Branched mPEG Derivative |
| 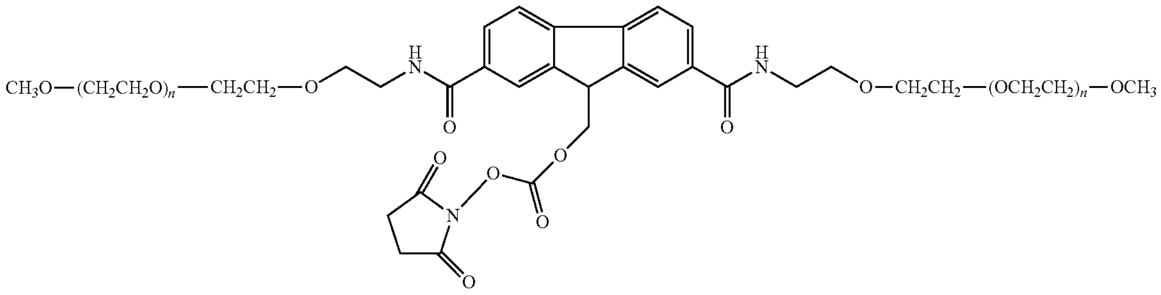<br>Branched mPEG Derivative |
| 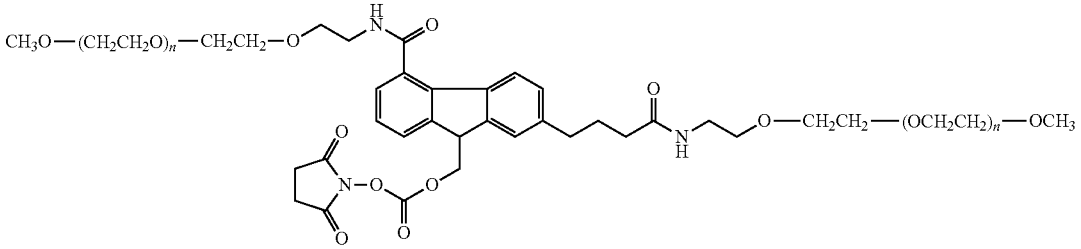<br>Branched mPEG Derivative |
| **Corresponding Conjugate** |
| $H_3CO-(CH_2CH_2O)_n-C(=O)-NH\text{-(IL-7)}$<br>Carbamate Linkage |
| $H_3CO-(CH_2CH_2O)_n-C(=O)-NH\text{-(IL-7)}$<br>Carbamate Linkage |
| $H_3CO-(CH_2CH_2O)_n-C(=O)-NH\text{-(IL-7)}$<br>Carbamate Linkage |
| $H_3C-(OCH_2CH_2)_n-O-CH_2-C(=O)-N\text{-(IL-7)}$<br>Amide Linkage |
| $\text{(IL-7)-}\underset{H}{N}-C(=O)-CH_2CH_2-(OCH_2CH_2)_n-O-CH_2CH_2-C(=O)-NH\text{-(IL-7)}$<br>Amide Linkages |

TABLE 1-continued
Amine-Selective Polymeric Reagents and the IL-7 Moiety Conjugate Formed Therefrom
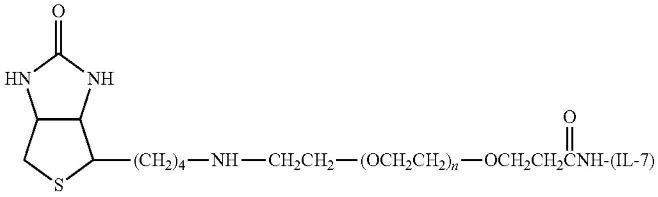
Amide Linkage
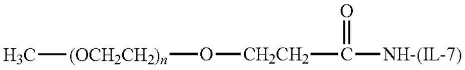
Amide Linkage
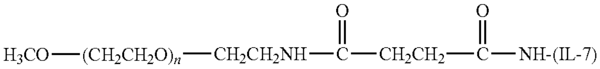
Amide Linkage
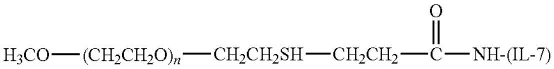
Amide Linkage
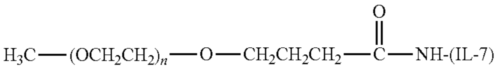
Amide Linkage
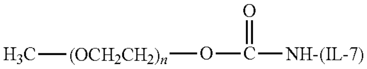
Carbamate Linkage
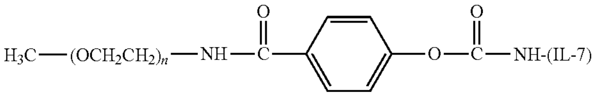
Carbamate Linkage
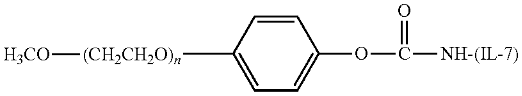
Carbamate Linkage
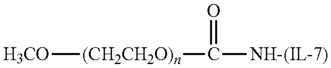
Carbamate Linkage
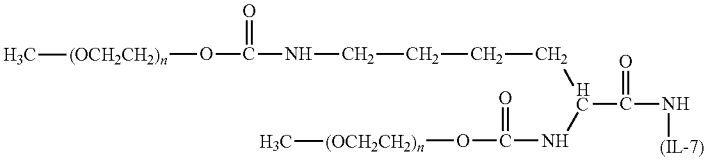
Amide Linkage TABLE 1-continued
Amine-Selective Polymeric Reagents and the IL-7 Moiety Conjugate Formed Therefrom
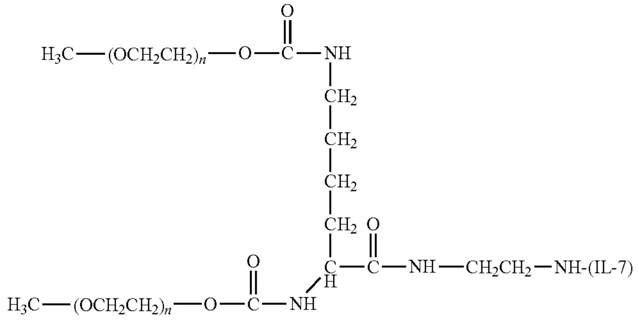
Secondary Amine Linkage
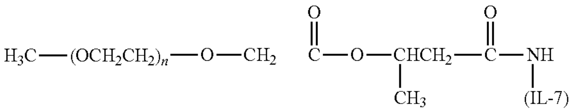
Amide Linkage
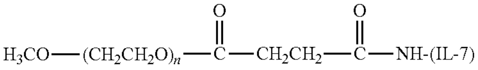
Amide Linkage
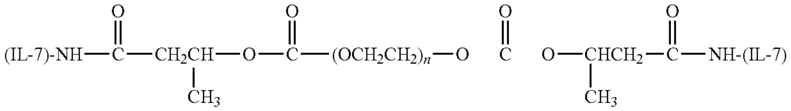
Amide Linkage
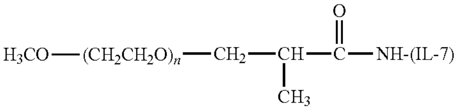
Amide Linkage
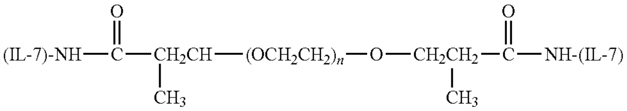
Amide Linkages
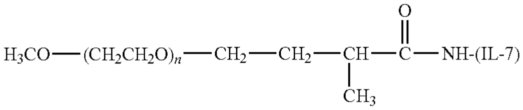
Amide Linkage
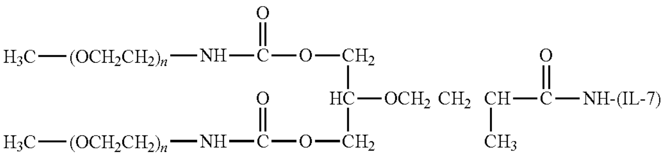
Amide Linkage TABLE 1-continued Amine-Selective Polymeric Reagents and the IL-7 Moiety Conjugate Formed Therefrom

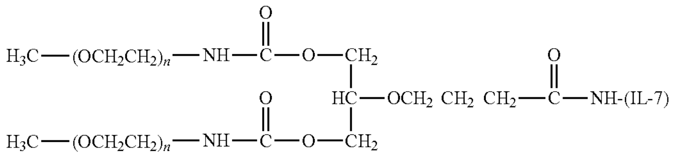

Amide Linkage

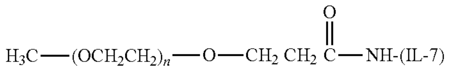

Amide Linkage (typically to IL-7 moiety haing an N-terminal cysteine or histidine)

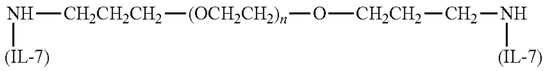

Secondary Amine Linkages $H_3C—(OCH_2CH_2)_n—O—CH_2CH_2—CH_2—NH\text{-(IL-7)}$

Secondary Amine Linkage

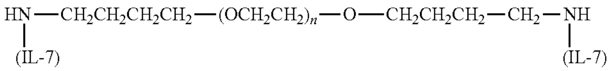

Secondary Amine Linkages $H_3C—(OCH_2CH_2)_n—O—CH_2CH_2CH_2—CH_2—NH\text{-(IL-7)}$ Secondary Amine Linkage

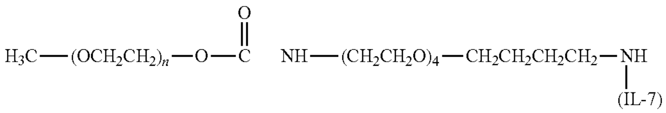

Secondary Amine Linkage

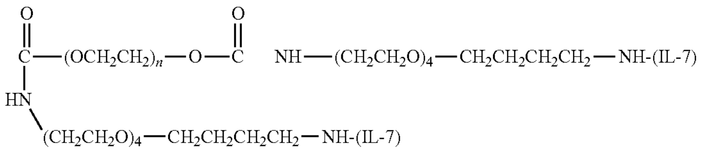

Secondary Amine Linkages

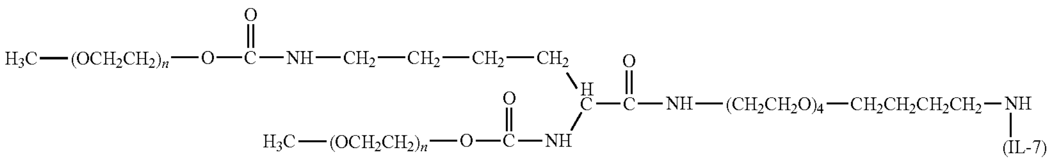

Secondary Amine Linkage

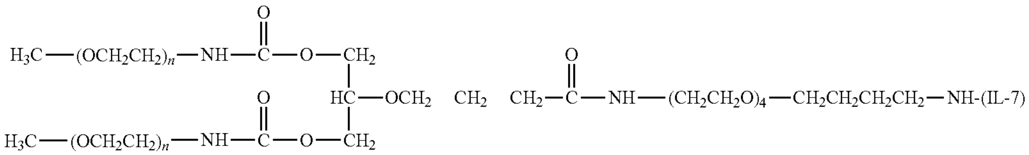

Secondary Amine Linkage

TABLE 1-continued

Amine-Selective Polymeric Reagents and the IL-7 Moiety Conjugate Formed Therefrom $H_3C—(OCH_2CH_2)_n—O—CH_2CH_2—NH\text{-(IL-7)}$ Secondary Amine Linkage

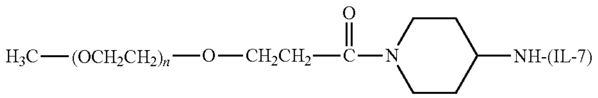

Secondary Amine Linkage
(to a secondary carbon)

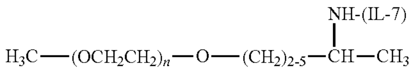

secondary Amine Linkage
(to a secondary carbon)

$H_3CO—(CH_2CH_2O)_n—CH_2CH_2—NH\text{-(IL-7)}$

Secondary Amine Linkage

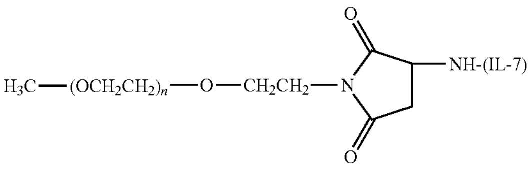

Secondary Amine Linkage

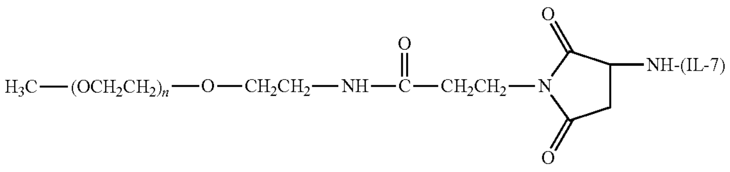

Secondary Amine Linkage

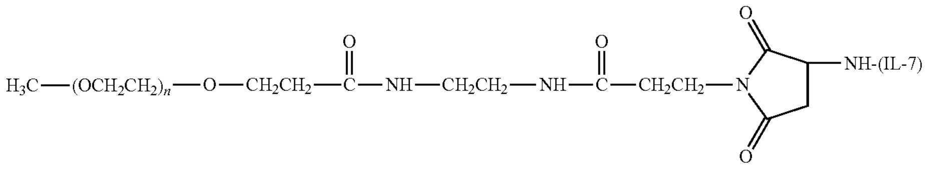

Secondary Amine Linkage

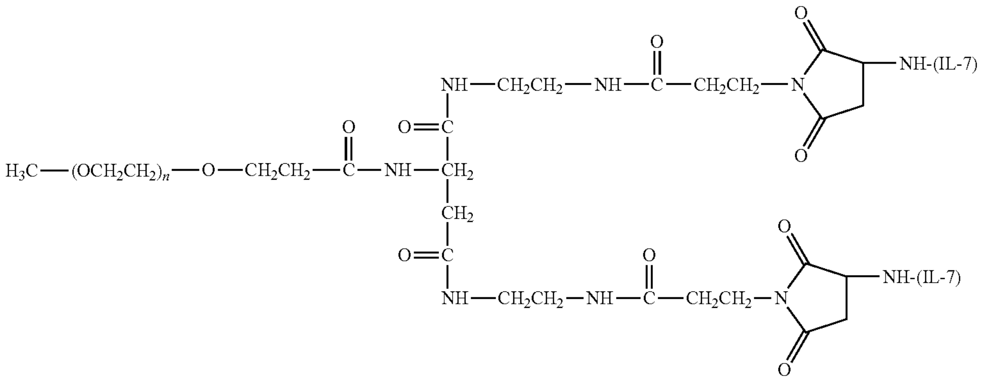

Secondary Amine Linkages

TABLE 1-continued
| Amine-Selective Polymeric Reagents and the IL-7 Moiety Conjugate Formed Therefrom |
|---|
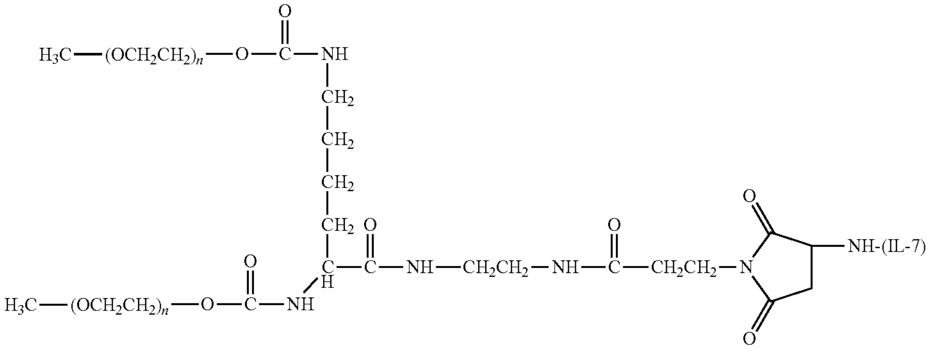
Secondary Amine Linkage
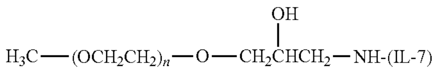
Secondary Amine Linkage
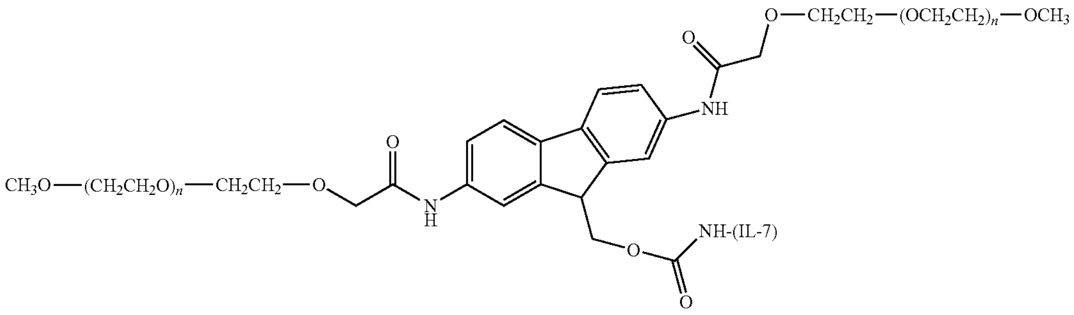
Releasable Linkage
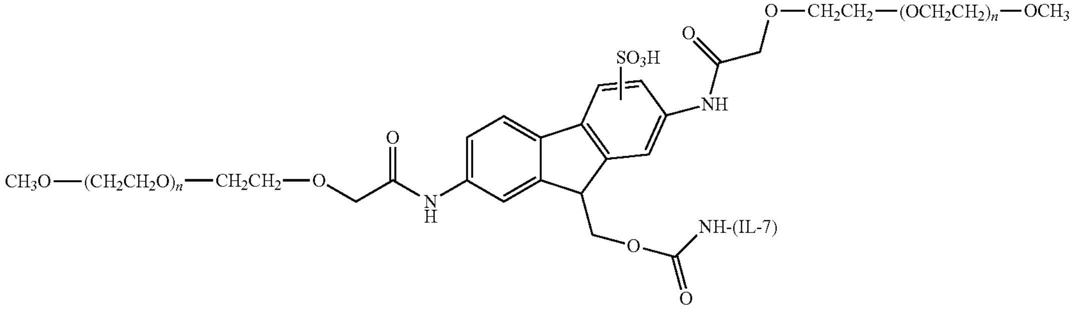
Releasable Linkage
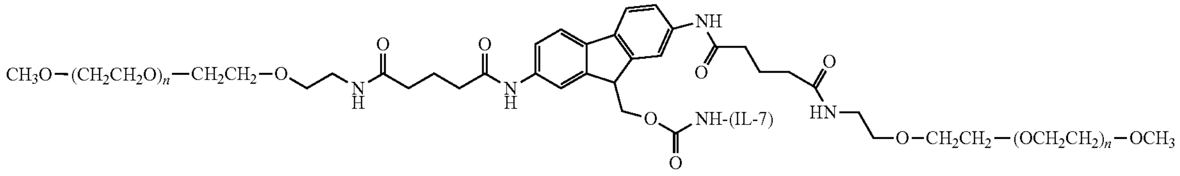
Releasable Linkage TABLE 1-continued

| Amine-Selective Polymeric Reagents and the IL-7 Moiety Conjugate Formed Therefrom |
|---|
| 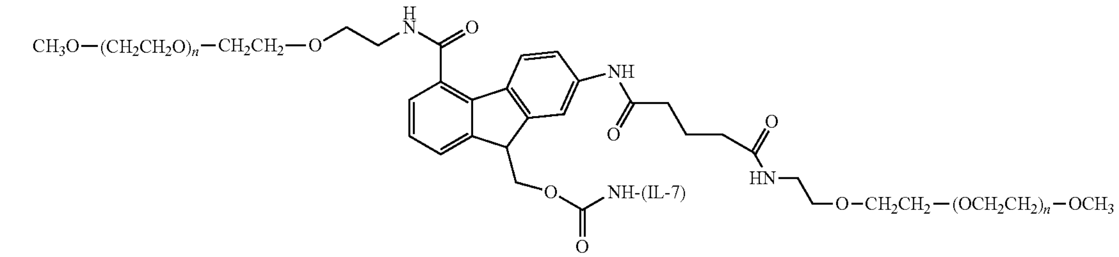 |
| Releasable Linkage |
| 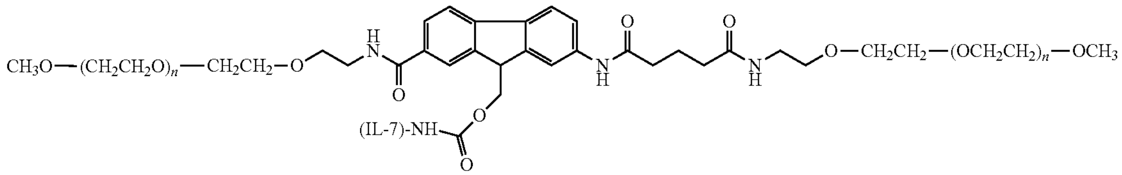 |
| Releasable Linkage |
| 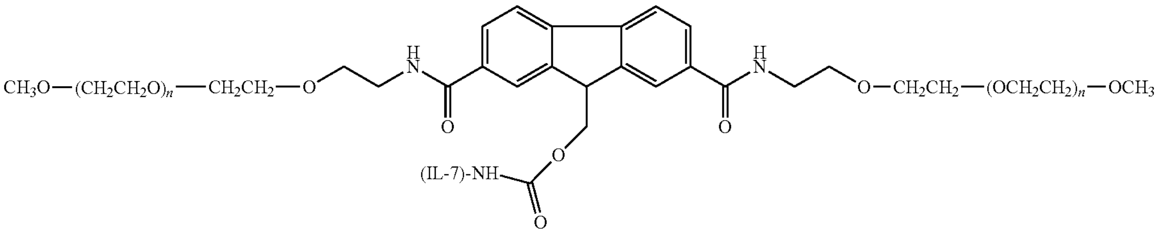 |
| Releasable Linkage |
| 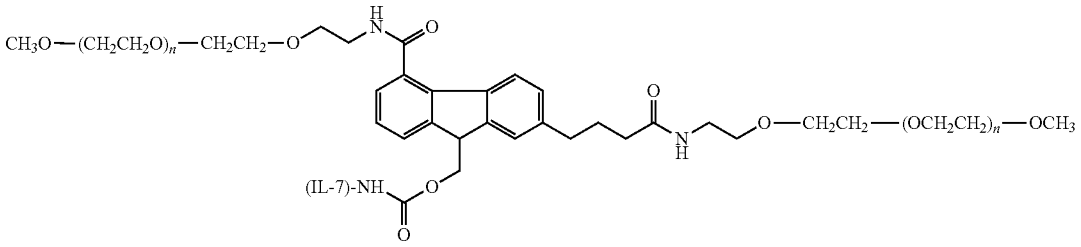 |
| Releasable Linkage |

Conjugation of a polymeric reagent to an amino group of an IL-7 moiety can be accomplished by a variety of techniques. In one approach, an IL-7 moiety can be conjugated to a polymeric reagent functionalized with a succinimidyl derivative (or other activated ester group, wherein approaches similar to those described for these alternative activated ester group-containing polymeric reagents can be used). In this approach, the polymer bearing a succinimidyl derivative can be attached to the IL-7 moiety in an aqueous media at a pH of 7 to 9.0, although using different reaction conditions (e.g., a lower pH such as 6 to 7, or different temperatures and/or less than 15° C.) can result in the attachment of the polymer to a different location on the IL-7 moiety. In addition, an amide linkage can be formed by reacting an amine-terminated non-peptidic, water-soluble polymer with an IL-7 moiety bearing an activating a carboxylic acid group.

Exemplary Conjugates are Encompassed within the Following Structure

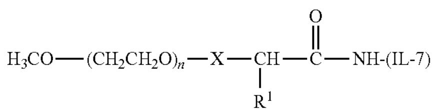

wherein:

(n) is an integer having a value of from 2 to 4000;

X is a spacer moiety;

$R^1$ is an organic radical; and

IL-7 is a residue of an IL-7 moiety.

Exemplary Conjugates are Encompassed by the Following Structure:

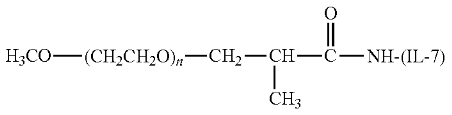

wherein (n) an integer having a value of from 2 to 4000 and IL-7 is a residue of an IL-7 moiety.

Typical of another approach useful for conjugating the IL-7 moiety to a polymeric reagent is use of reductive amination to conjugate a primary amine of an IL-7 moiety with a polymeric reagent functionalized with a ketone, aldehyde or a hydrated form thereof (e.g., ketone hydrate, aldehyde hydrate). In this approach, the primary amine from the IL-7 moiety reacts with the carbonyl group of the aldehyde or ketone (or the corresponding hydroxyl-containing group of a hydrated aldehyde or ketone), thereby forming a Schiff base. The Schiff base, in turn, can then be reductively converted to a stable conjugate through use of a reducing agent such as sodium borohydride. Selective reactions (e.g., at the N-terminus) are possible, particularly with a polymer functionalized with a ketone or an alpha-methyl branched aldehyde and/or under specific reaction conditions (e.g., reduced pH).

Exemplary conjugates of the invention wherein the water-soluble polymer is in a branched form include those wherein the water-soluble polymer is encompassed within the following structure:

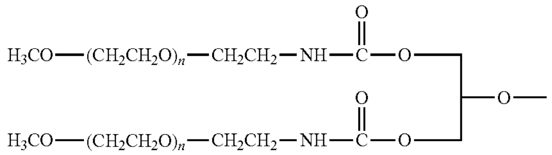

wherein each (n) is independently an integer having a value of from 2 to 4000.

Exemplary conjugates of the invention are encompassed within the following structure:

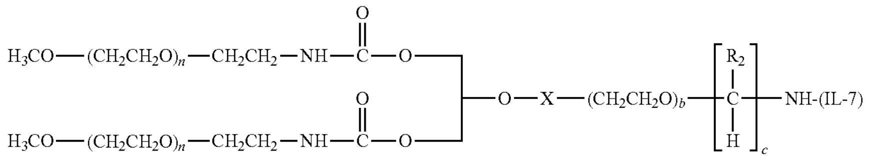

wherein:

each (n) is independently an integer having a value of from 2 to 4000;

X is spacer moiety;

(b) is an integer having a value 2 through 6;

(c) is an integer having a value 2 through 6;

$R^2$, in each occurrence, is independently H or lower alkyl; and

IL-7 is a residue of an IL-7 moiety.

Exemplary Conjugates of the Invention are Encompassed within the Following Structure:

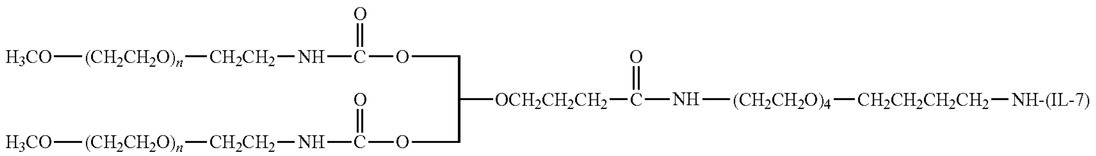

wherein:

each (n) is independently an integer having a value of from 2 to 4000; and

IL-7 is a residue of an IL-7 moiety.

Other exemplary conjugates of the invention are encompassed within following structure:

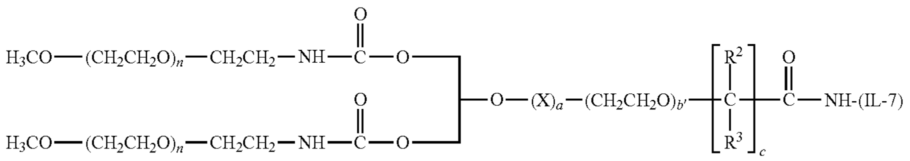

wherein:

each (n) is independently an integer having a value of from 2 to 4000;

(a) is either zero or one;

X, when present, is a spacer moiety comprised of one or more atoms;

(b') is zero or an integer having a value of one through ten;

(c) is an integer having a value of one through ten;

$R^2$, in each occurrence, is independently H or an organic radical;

$R^3$, in each occurrence, is independently H or an organic radical; and

IL-7 is a residue of an IL-7 moiety.

Still further exemplary conjugates of the invention are encompassed within the following structure:

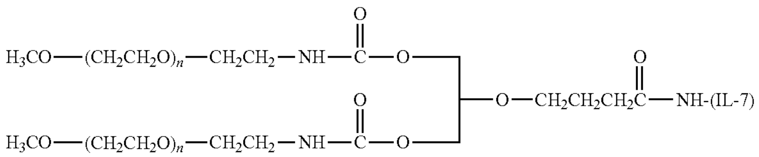

wherein:

each (n) is independently an integer having a value of from 2 to 4000; and

IL-7 is a residue of IL-7 moiety.

Exemplary conjugates that include a releasable linkage include those in which an IL-7 moiety are conjugated to a polymeric reagent encompassed within the following formula:

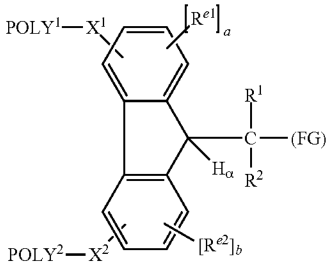

wherein:

$POLY^1$ is a first water-soluble polymer;

$POLY^2$ is a second water-soluble polymer;

$X^1$ is a first spacer moiety;

$X^2$ is a second spacer moiety;

$H_\alpha$ is an ionizable hydrogen atom;

$R^1$ is H or an organic radical;

$R^2$ is H or an organic radical;

(a) is either zero or one;

(b) is either zero or one;

$R^{e1}$, when present, is a first electron altering group;

$R^{e2}$, when present, is a second electron altering group; and (FG) is a functional group capable of reacting with an amino group of an active agent to form a releasable linkage, such as a carbamate linkage. Within this formula, polymeric reagents having the more defined structure are contemplated:

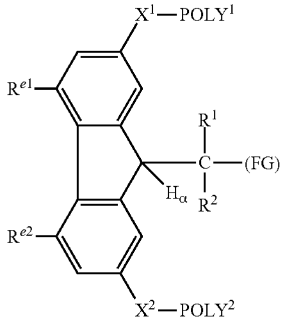

wherein each of $POLY^1$, $POLY^2$, $X^1$, $X^2$, $R^1$, $R^2$, $H_\alpha$ and (FG) is as previously defined, and $R^{e1}$ is a first electron altering group; and $R^{e2}$ is a second electron altering group.

Still further exemplary polymeric reagents fall within the following formulae:

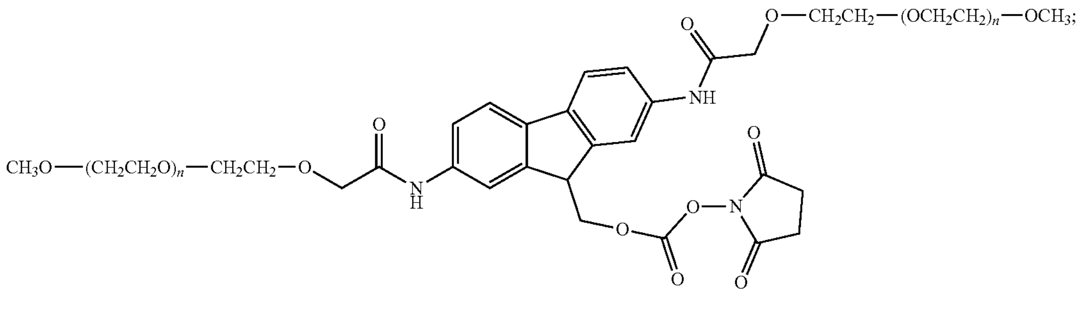

-continued
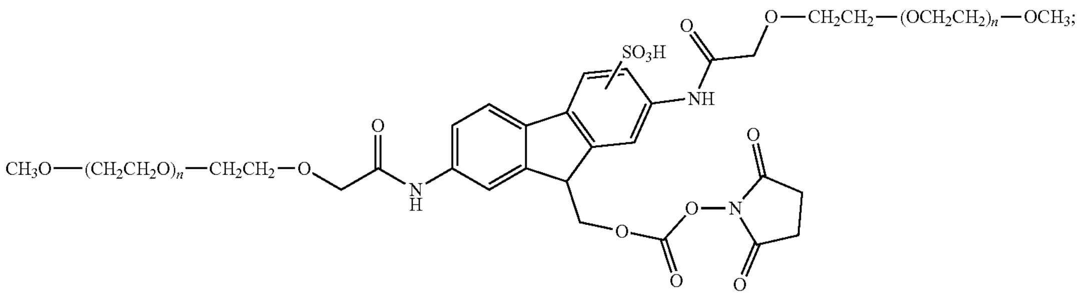
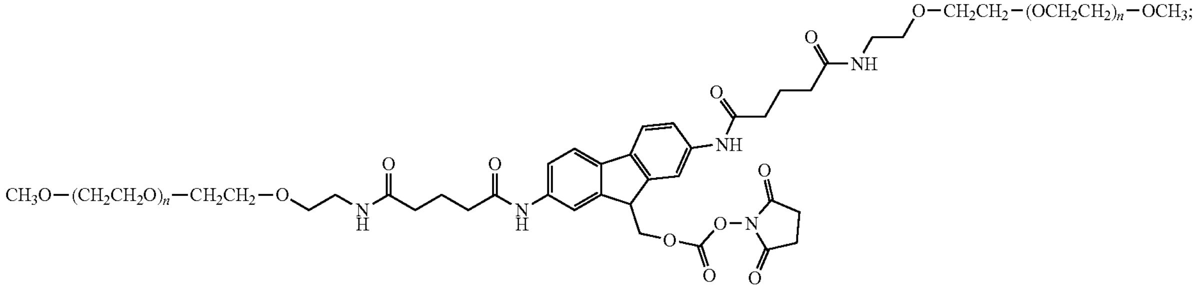
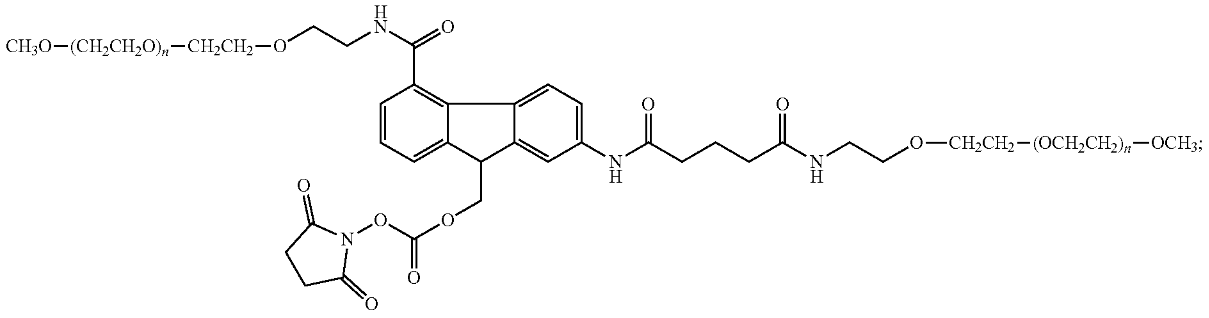
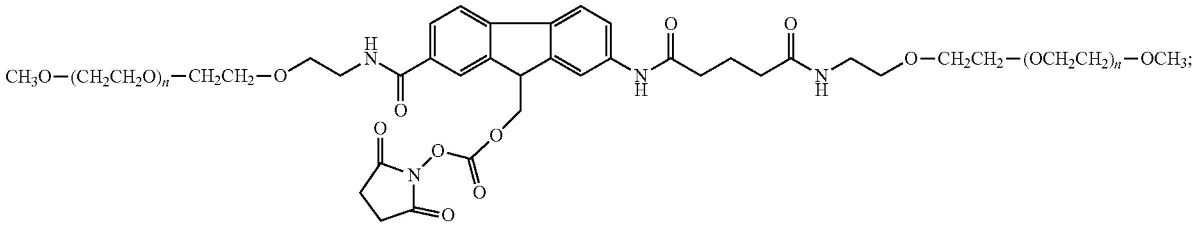
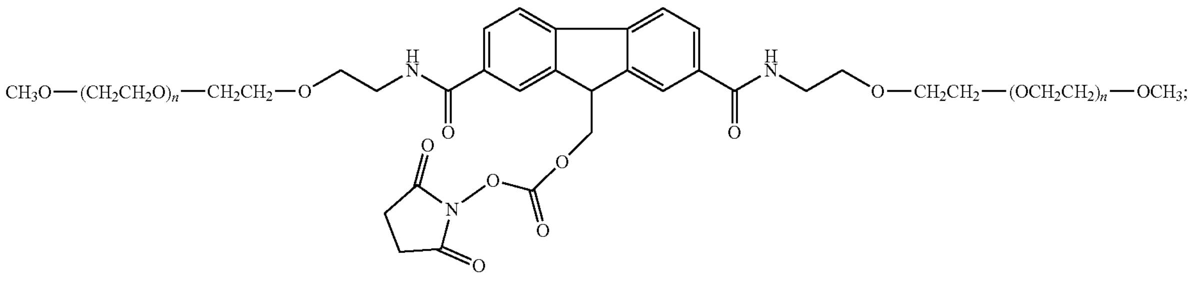
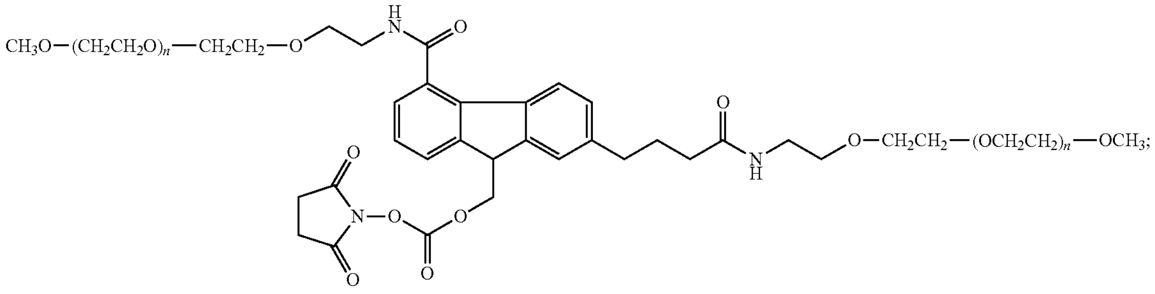
and -continued

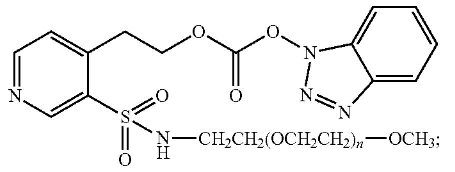

wherein, for each structure and in each instance, (n) is independently an integer from 4 to 1500.

These releasable linkage-providing polymeric reagents can be prepared in accordance with the procedures set forth in U.S. Patent Application Publication No. 2006/0293499.

Exemplary conjugates formed using releasable linkage-providing polymeric reagents include those of the following formulae:

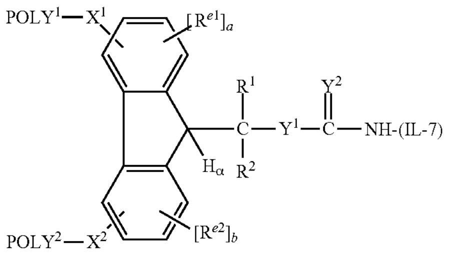

wherein:

$POLY^1$ is a first water-soluble polymer;

$POLY^2$ is a second water-soluble polymer;

$X^1$ is a first spacer moiety;

$X^2$ is a second spacer moiety;

$H_a$ is an ionizable hydrogen atom;

$R^1$ is H or an organic radical;

$R^2$ is H or an organic radical;

(a) is either zero or one;

(b) is either zero or one;

$R^{e1}$, when present, is a first electron altering group;

$R^{e2}$, when present, is a second electron altering group;

$Y^1$ is O or S;

$Y^2$ is O or S; and

IL-7 is a residue of an IL-7 moiety.

Exemplary Conjugates have the Following Structure:

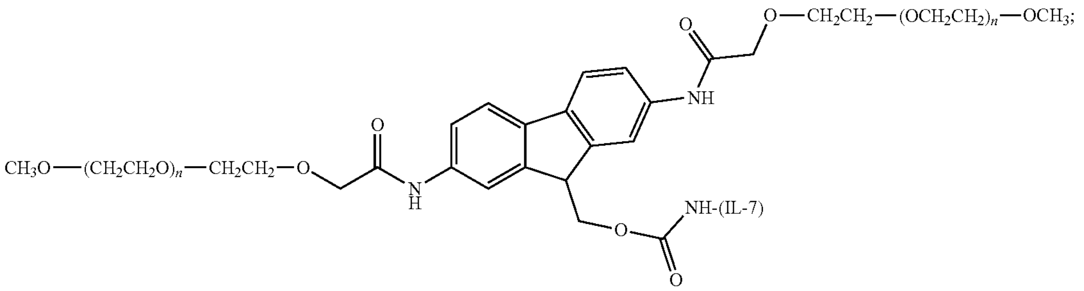

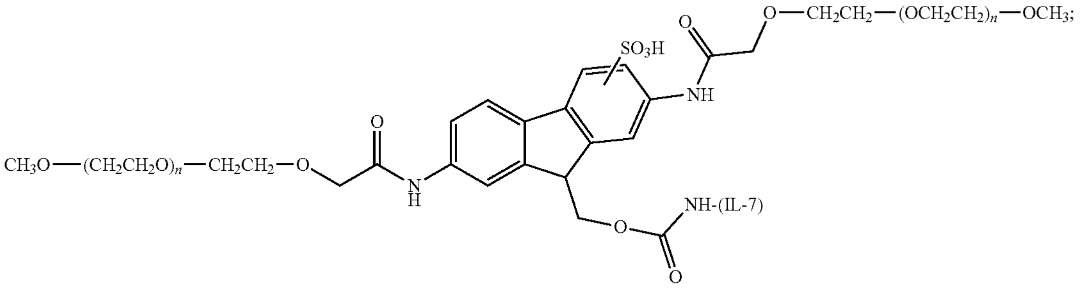

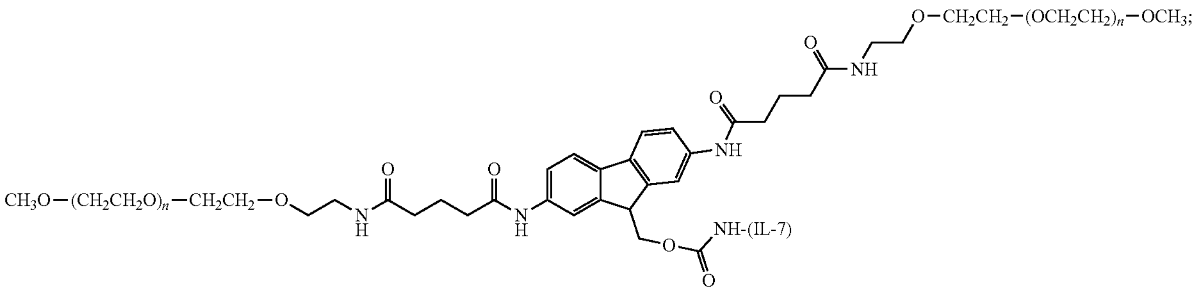

-continued

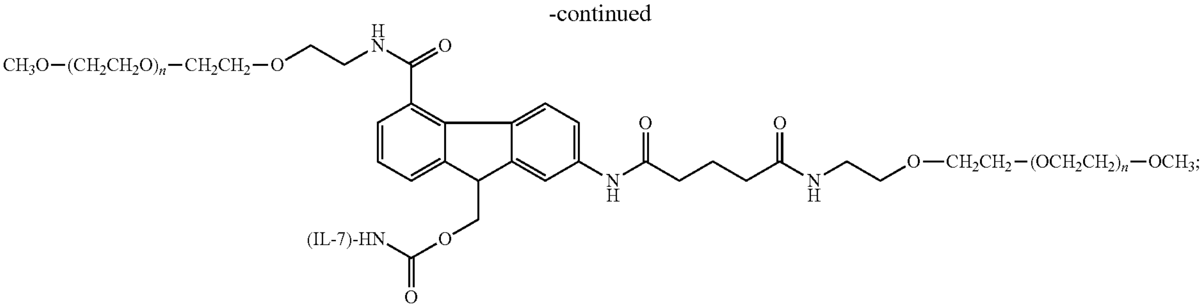

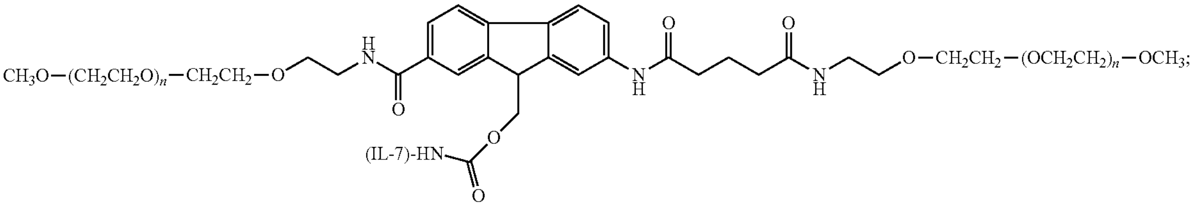

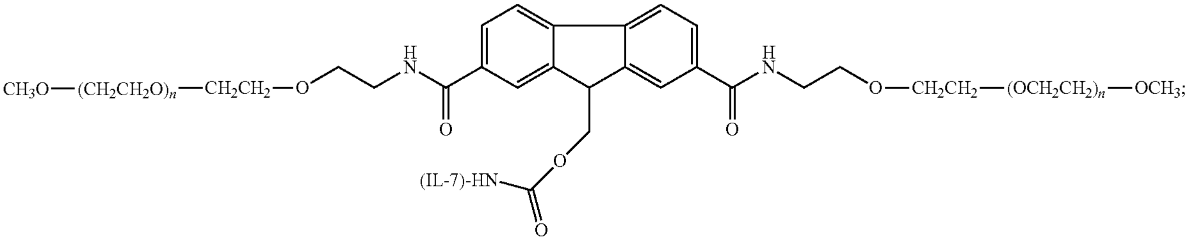

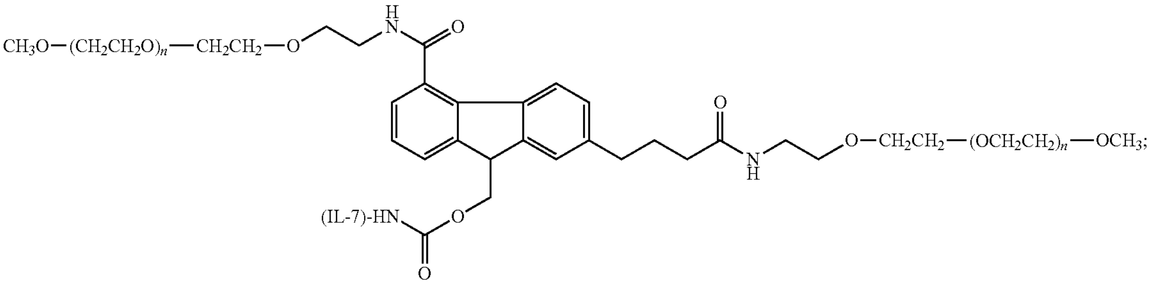

and

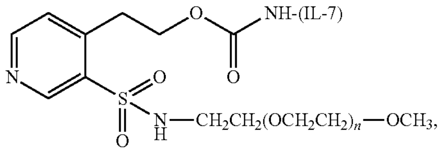

wherein, for each structure and in each instance, (n) is independently an integer from 4 to 1500, and IL-7 is a residue of an IL-7 moiety.

Carboxyl groups represent another functional group that can serve as a point of attachment on the IL-7 moiety. Structurally, the conjugate will comprise the following:

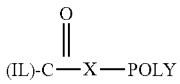

where IL-7 and the adjacent carbonyl group corresponds to the carboxyl-containing IL-7 moiety, X is a linkage, preferably a heteroatom selected from O, N(H), and S, and POLY is a water-soluble polymer such as PEG, optionally terminating in an end-capping moiety.

The C(O)—X linkage results from the reaction between a polymeric derivative bearing a terminal functional group and a carboxyl-containing IL-7 moiety. As discussed above, the specific linkage will depend on the type of functional group utilized. If the polymer is end-functionalized or "activated" with a hydroxyl group, the resulting linkage will be a carboxylic acid ester and X will be O. If the polymer backbone is functionalized with a thiol group, the resulting linkage will be a thioester and X will be S. When certain multi-arm, branched or forked polymers are employed, the C(O)X moiety, and in particular the X moiety, may be relatively more complex and may include a longer linkage structure.

Water-soluble derivatives containing a hydrazide moiety are also useful for conjugation at a carbonyl and carboxylic acid. To the extent that the IL-7 moiety does not contain a carbonyl moiety or a carboxylic acid, one can be added using techniques known to one of ordinary skill in the art. For example, a carbonyl moiety can be introduced by reducing a carboxylic acid (e.g., the C-terminal carboxylic acid) and/or by providing glycosylated or glycated (wherein the added sugars have a carbonyl moiety) versions of the IL-7 moiety. With respect to IL-7 moieties containing a carboxylic acid, a PEG-hydrazine reagent can, in the presence of a coupling agent (e.g., DCC), covalently attach to the IL-7 moiety [e.g., mPEG-$OCH_2C(O)NHNH_2$+HOC(O)-(IL-7) results in mPEG-$OCH_2C(O)NHNHC(O)$-IL-7]. Specific examples of water-soluble derivatives containing a hydrazide moiety, along with the corresponding conjugates, are provided in Table 2, below. In addition, any water-soluble derivative containing an activated ester (e.g., a succinimidyl group) can be converted to contain a hydrazide moiety by reacting the water-soluble polymer derivative containing the activated ester with hydrazine ($NH_2$—$NH_2$) or tert-butyl carbazate [$NH_2NHCO_2C(CH_3)_3$]. In the table, the variable (n) represents the number of repeating monomeric units and "—C(O)-(IL-7)" represents the residue of the IL-7 moiety following conjugation to the polymeric reagent. Optionally, the hydrazone linkage can be reduced using a suitable reducing agent. While each polymeric portion [e.g., $(OCH_2CH_2)_n$ or $(CH_2CH_2O)_n$] presented in Table 2 terminates in a "$CH_3$" group, other groups (such as H and benzyl) can be substituted therefor.

Table 2

| Carboxyl-Specific Polymeric Reagents and the IL-7 Moiety Conjugate Formed Therefrom |
|---|
| Polymeric Reagent |
| 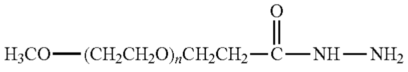 mPEG-Hydrazine Reagents |
| 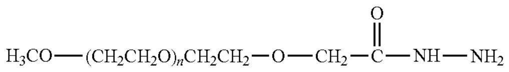 mPEG-Hydrazine Reagents |
| 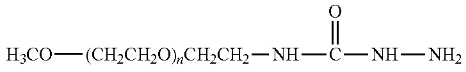 mPEG-Hydrazine Reagents |
| 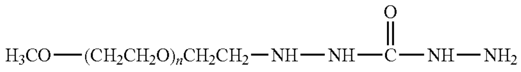 mPEG-Hydrazine Reagents |
| 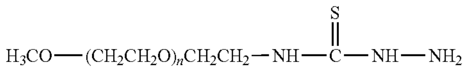 mPEG-Hydrazine Reagents |
| 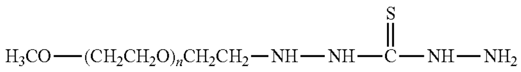 mPEG-Hydrazine Reagents |
| 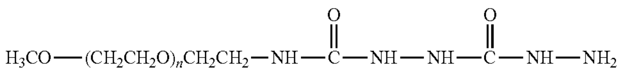 mPEG-Hydrazine Reagents |
| 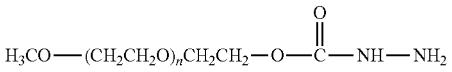 mPEG-Hydrazine Reagents |
| 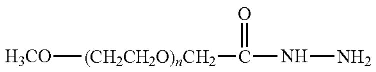 mPEG-Hydrazine Reagents |

Table 2-continued

| Carboxyl-Specific Polymeric Reagents and the IL-7 Moiety Conjugate Formed Therefrom |
|---|
| Corresponding Conjugate |
| 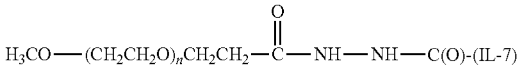 Hydrazone Linkage |
| 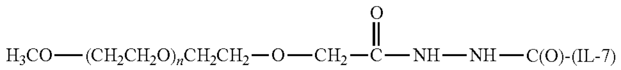 Hydrazone Linkage |
| 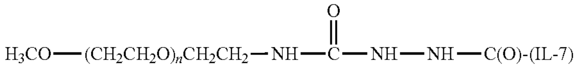 Hydrazone Linkage |
| 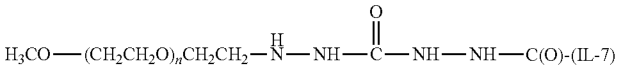 Hydrazone Linkage |
| 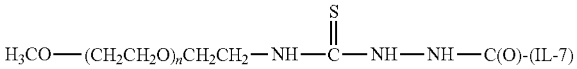 Hydrazone Linkage |
| 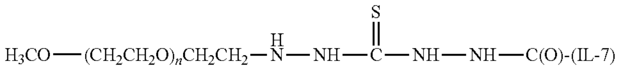 Hydrazone Linkage |
| 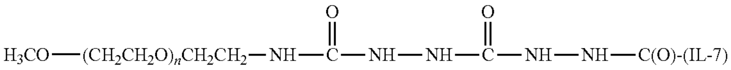 Hydrazone Linkage |
| 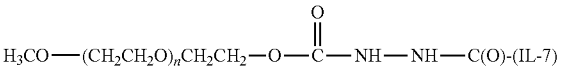 Hydrazone Linkage |
| 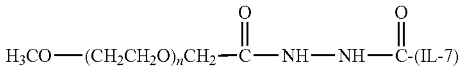 C(O)NHNHC(O) Linkage |

Thiol groups contained within the IL-7 moiety can serve as effective sites of attachment for the water-soluble polymer. In particular, cysteine residues provide thiol groups when the IL-7 moiety is a protein. The thiol groups in such cysteine residues can then be reacted with an activated PEG that is specific for reaction with thiol groups, e.g., an N-maleimidyl polymer or other derivative as described in U.S. Pat. No. 5,739,208 and in WO 01/62827. In addition, a protected thiol may be incorporated into an oligosaccharide side chain of an activated glycoprotein, followed by deprotection with a thiol-reactive water-soluble polymer.

Specific examples of reagents, along with the corresponding conjugate, are provided in Table 3, below. In the table, the variable (n) represents the number of repeating monomeric units and "—S-(IL-7)" represents the IL-7 moiety residue following conjugation to the water-soluble polymer. While each polymeric portion [e.g., $(OCH_2CH_2)_n$ or $(CH_2CH_2O)_n$] presented in Table 3 terminates in a "$CH_3$" group, other groups (such as H and benzyl) can be substituted therefor.

With respect to SEQ ID NO: 1 corresponding to an exemplary IL-7 moiety, it can be seen that there are cysteine residues at position 3, 35, 48, 93, 130 and 142. Thus, exemplary thiol attachment sites include position 3, 35, 48, 93, 130 and 142. In addition, it is possible to add a cysteine residue to the IL-7 moiety using conventional synthetic techniques. See, for example, the procedure described in WO 90/12874 for adding cysteine residues, wherein such procedure can be adapted for an IL-7 moiety. In addition, conventional genetic engineering processes can also be used to introduce a cysteine residue into the IL-7 moiety. In some embodiments, however, it is preferred not to introduce an additional cysteine residue and/or thiol group.

Table 3
| Thiol-Selective Polymeric Reagents and the IL-7 Moiety Conjugate Formed Therefrom |
|---|
| Polymeric Reagent |
| 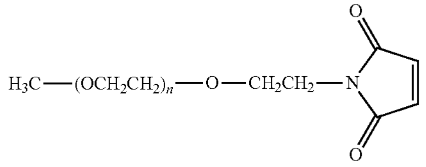 |
| mPEG Maleimide Reagent |
| 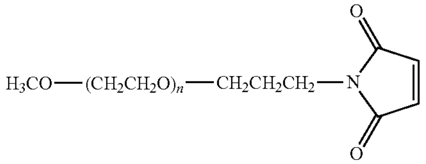 |
| mPEG Maleimide Reagent |
| 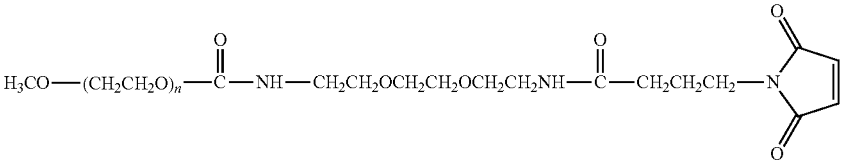 |
| mPEG Maleimide Reagent |
| 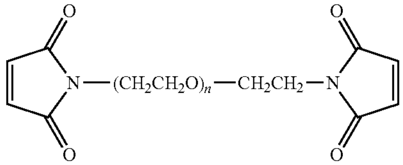 |
| Homobifunctional mPEG Maleimide Reagent |
| 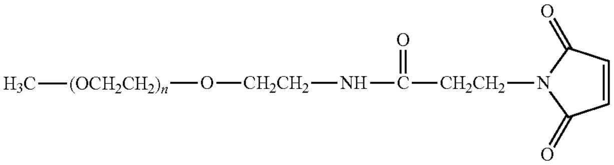 |
| mPEG Maleimide Reagent |
| 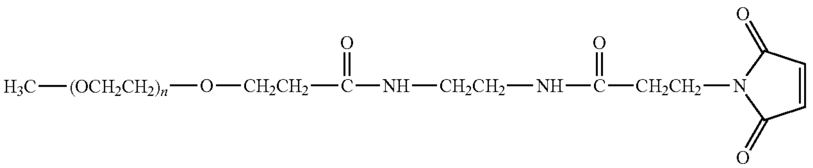 |
| mPEG Maleimide Reagent |
| 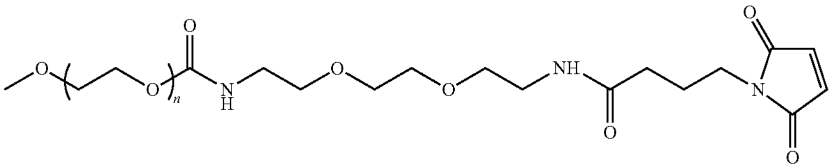 |
| mPEG Maleimide Reagent |

Table 3-continued
Thiol-Selective Polymeric Reagents and the IL-7 Moiety Conjugate Formed Therefrom
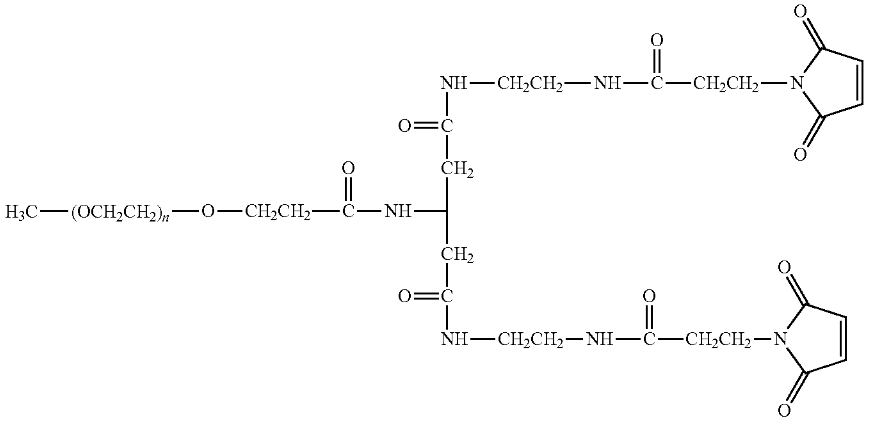
mPEG Forked Maleimide Reagent
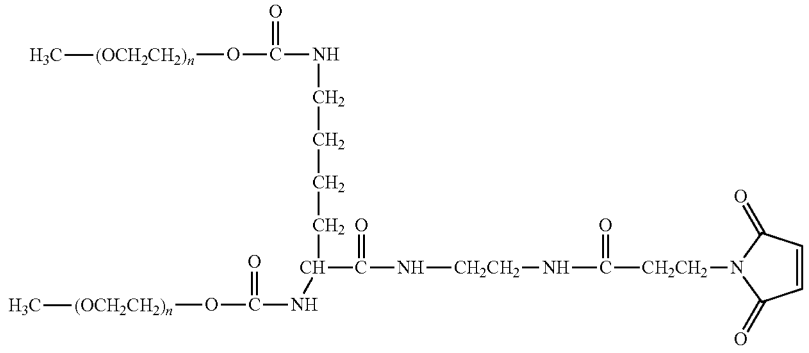
branched mPEG2 Maleimide Reagent
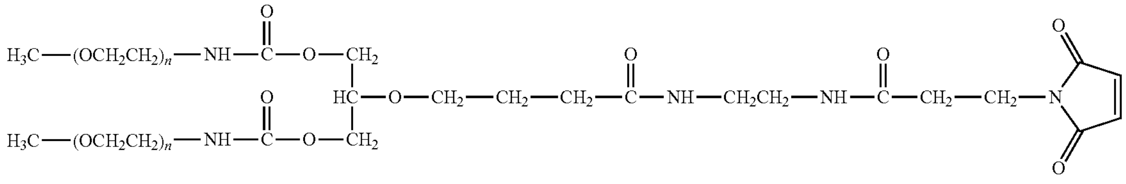
branched mPEG2 Maleimide Reagent
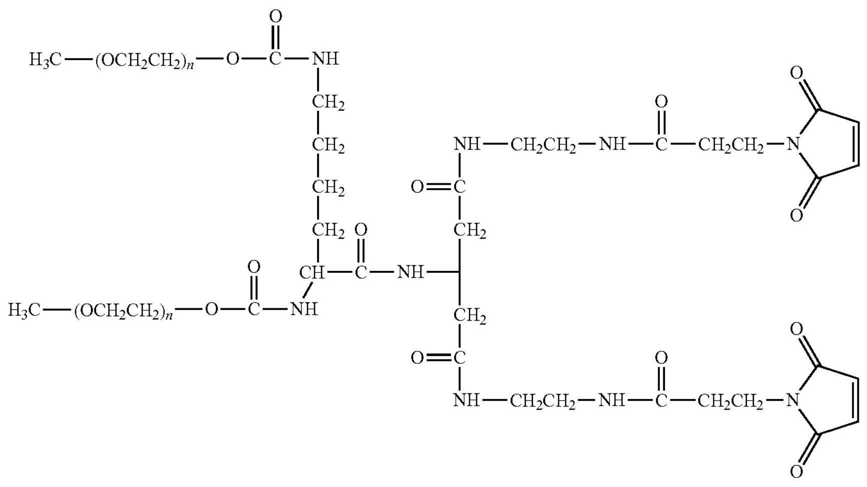

Table 3-continued

| Thiol-Selective Polymeric Reagents and the IL-7 Moiety Conjugate Formed Therefrom |
|---|
| Branched mPEG2 Forked Maleimide Reagent<br>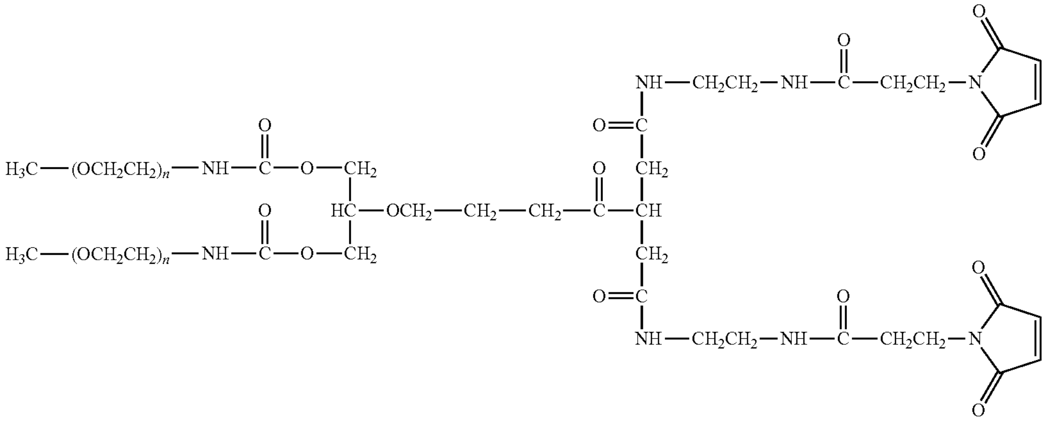<br>Branched mPEG2 Forked Maleimide Reagent |
| 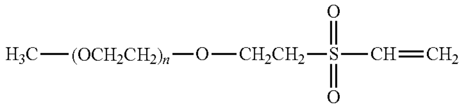<br>mPEG Vinyl Sulfone Reagent |
| 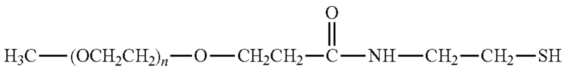<br>mPEG Thiol Reagent |
| 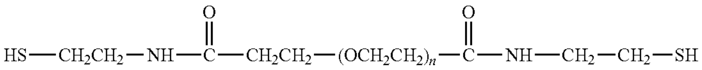<br>Homobifunctional PEG Thiol Reagent |
| 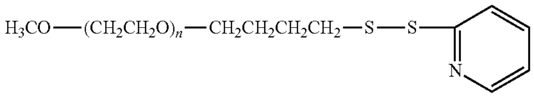<br>mPEG Disulfide Reagent |
| 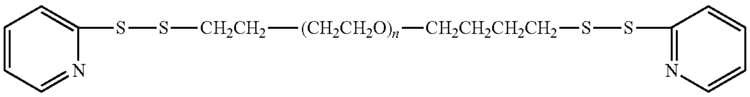<br>Homobifunctional Disulfide Reagent |
| **Corresponding Conjugate** |
| 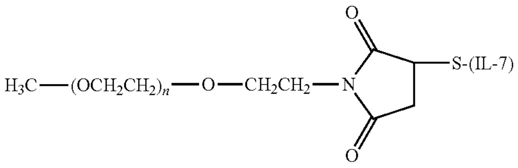<br>Thioether Linkage |

Table 3-continued
Thiol-Selective Polymeric Reagents and the IL-7 Moiety Conjugate Formed Therefrom
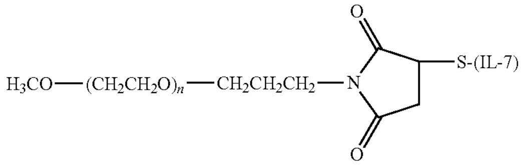
Thioether Linkage
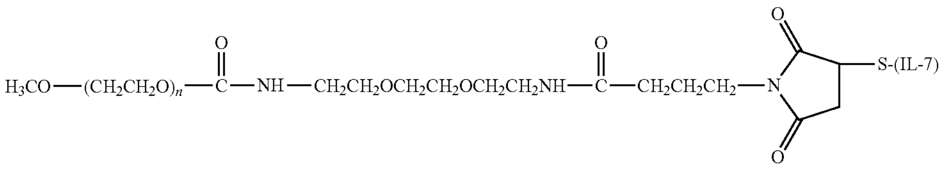
Thioether Linkage
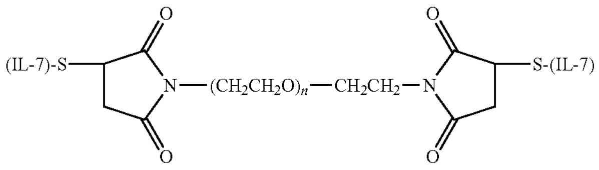
Thioether Linkage
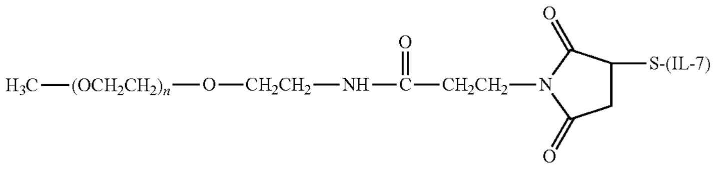
Thioether Linkage
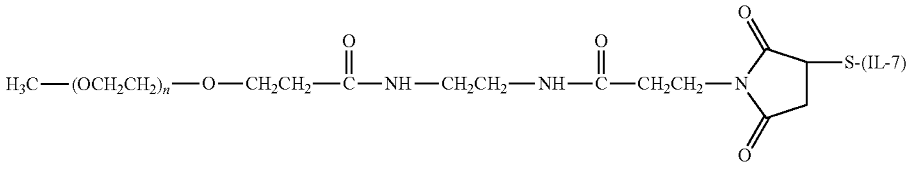
Thioether Linkage
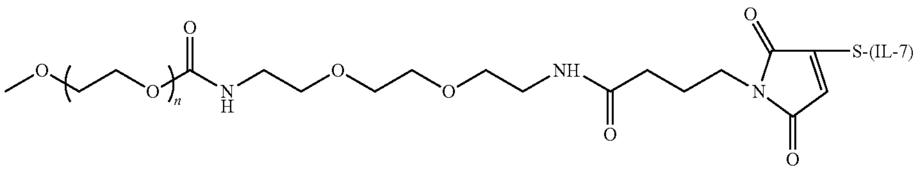
Thioether Linkage Table 3-continued
Thiol-Selective Polymeric Reagents and the IL-7 Moiety Conjugate Formed Therefrom
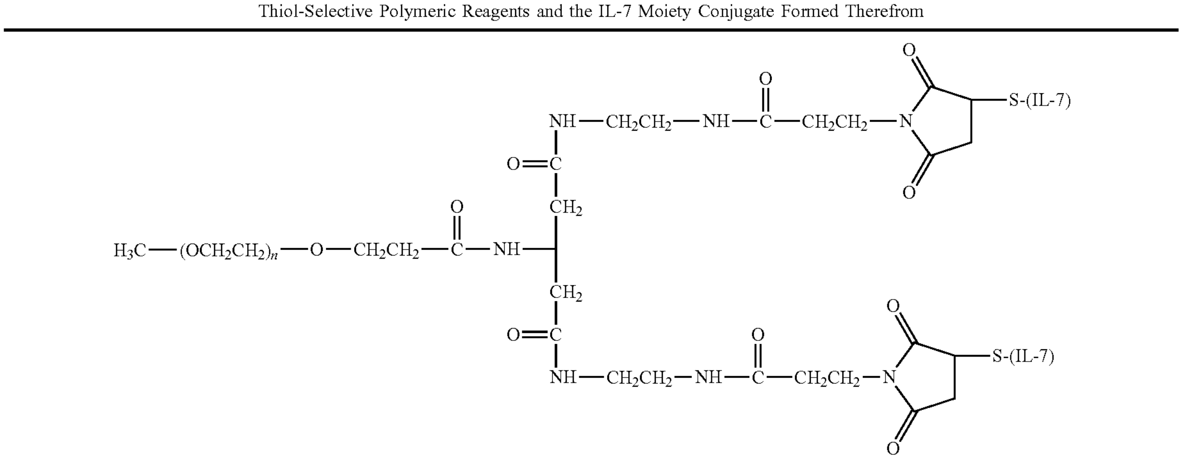
Thioether Linkage
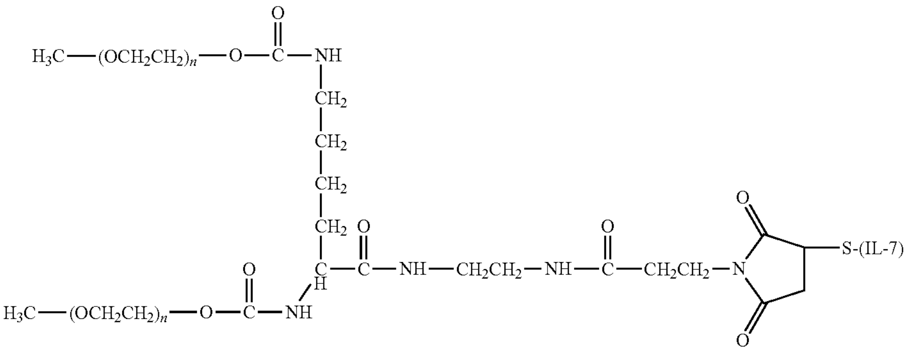
Thioether Linkage
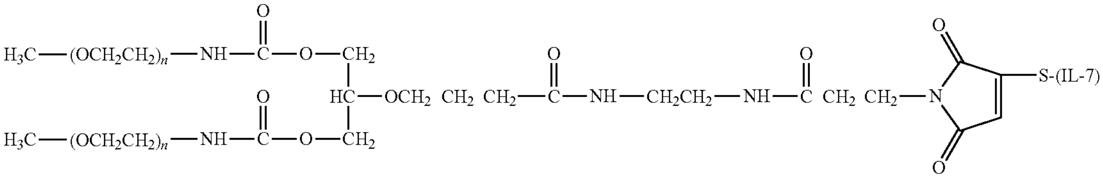
Thioether Linkage
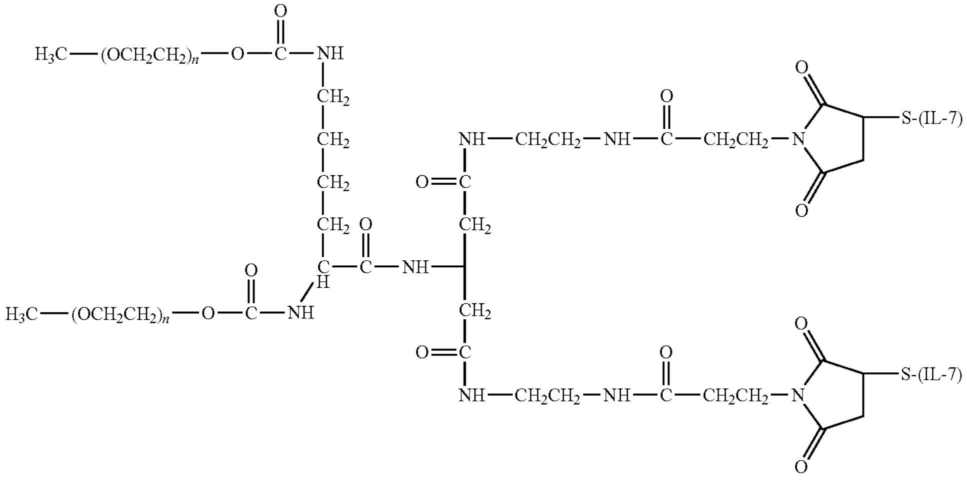
Thioether Linkage Table 3-continued Thiol-Selective Polymeric Reagents and the IL-7 Moiety Conjugate Formed Therefrom

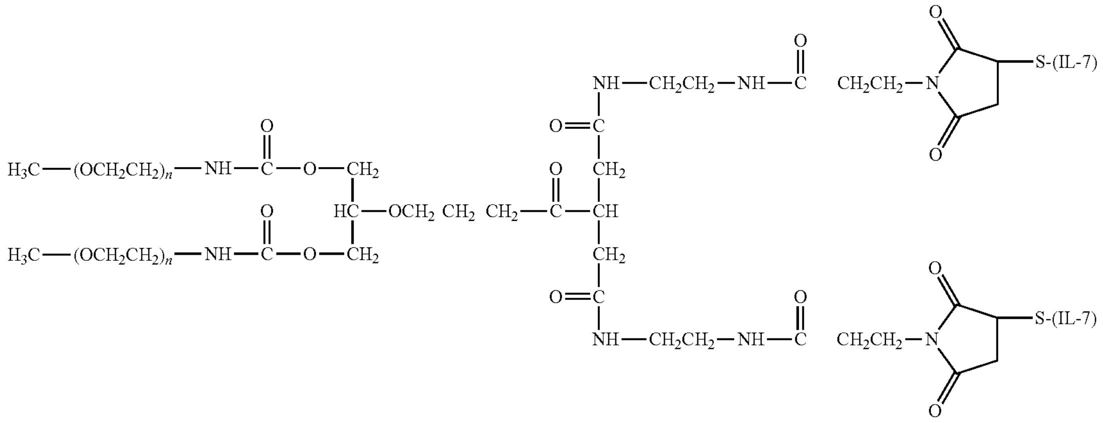

Thioether Linkage

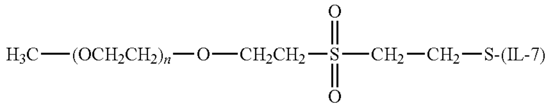

Thioether Linkage

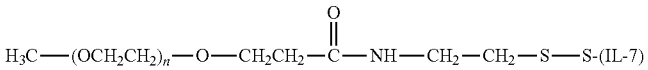

Disulfide Linkage

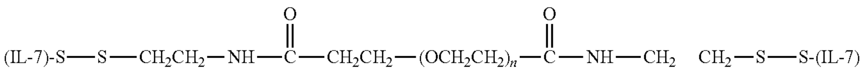

Disulfide Linkage $H_3CO—(CH_2CH_2O)_n—CH_2CH_2CH_2CH_2—S—S$-(IL-7)

Disulfide Linkage (IL-7)-$S—S—CH_2CH_2—(CH_2CH_2O)_n—CH_2CH_2CH_2CH_2—S—S$-(IL-7)

Disulfide Linkage

With respect to conjugates formed from water-soluble polymers bearing one or more maleimide functional groups (regardless of whether the maleimide reacts with an amine or thiol group on the IL-7 moiety), the corresponding maleamic acid form(s) of the water-soluble polymer can also react with the IL-7 moiety. Under certain conditions (e.g., a pH of about 7-9 and in the presence of water), the maleimide ring will "open" to form the corresponding maleamic acid. The maleamic acid, in turn, can react with an amine or thiol group of an IL-7 moiety. Exemplary maleamic acid-based reactions are schematically shown below. POLY represents the water-soluble polymer, and IL-7 represents the IL-7 moiety.

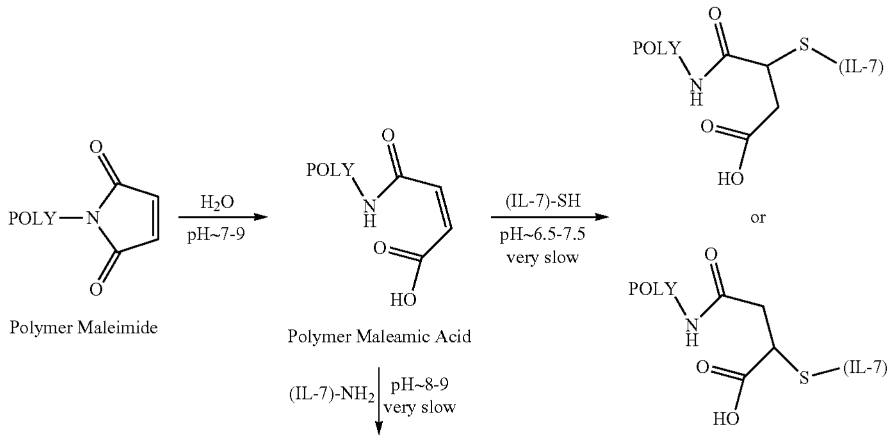

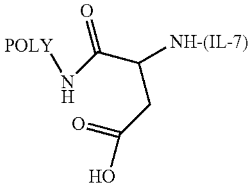

or

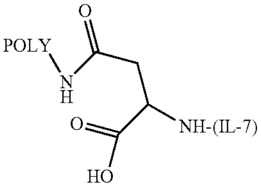

A representative conjugate in accordance with the invention can have the following structure:

$$POLY-L_{0,1}-C(O)Z—Y—S—S-(IL-7)$$

wherein POLY is a water-soluble polymer, L is an optional linker, Z is a heteroatom selected from the group consisting of 0, NH, and S, and Y is selected from the group consisting of $C_{2-10}$ alkyl, $C_{2-10}$ substituted alkyl, aryl, and substituted aryl, and IL-7 is an IL-7 moiety. Polymeric reagents that can be reacted with an IL-7 moiety and result in this type of conjugate are described in U.S. Patent Application Publication No. 2005/0014903.

As previously indicated, exemplary conjugates of the invention wherein the water-soluble polymer is in a branched form, will have the branched form of the water-soluble polymer comprise the following structure:

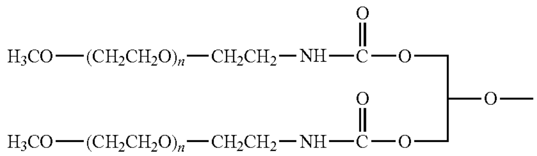

wherein each (n) is independently an integer having a value of from 2 to 4000.

Exemplary conjugates having a water-soluble polymer in branched form are prepared using the following reagent:

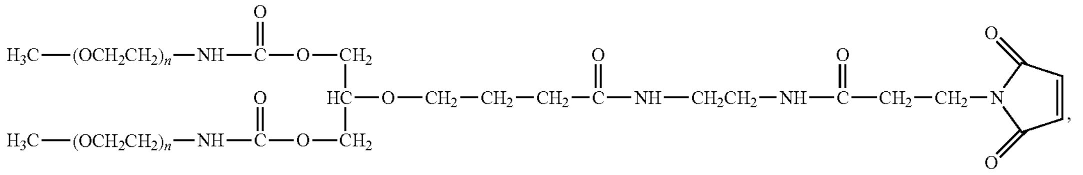

thereby forming a conjugate having the following structure:

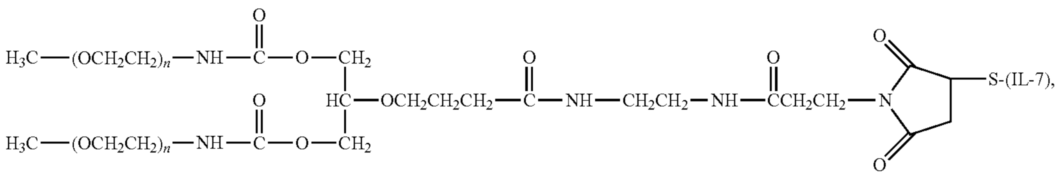

wherein:

(for each structure) each (n) is independently an integer having a value of from 2 to 4000; and IL-7 is a residue of IL-7 moiety.

An Additional Exemplary Conjugate can be Formed Using a Reagent:

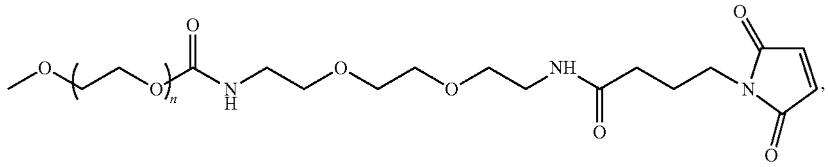

thereby forming a conjugate having the following structure:

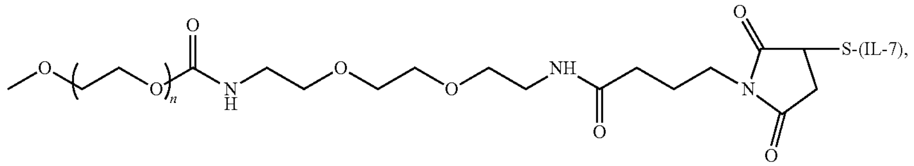

wherein:

(for each structure) (n) is independently an integer having a value of from 2 to 4000; and IL-7 is a residue of IL-7 moiety.

Conjugates can be formed using thiol-selective polymeric reagents in a number of ways and the invention is not limited in this regard. For example, the IL-7 moiety—optionally in a suitable buffer (including amine-containing buffers, if desired)—is placed in an aqueous media at a pH of about 7-8 and the thiol-selective polymeric reagent is added at a molar excess. The reaction is allowed to proceed for about 0.5 to 2 hours, although reaction times of greater than 2 hours (e.g., 5 hours, 10 hours, 12 hours, and 24 hours) can be useful if PEGylation yields are determined to be relatively low. Exemplary polymeric reagents that can be used in this approach are polymeric reagents bearing a reactive group selected from the group consisting of maleimide, sulfone (e.g., vinyl sulfone), and thiol (e.g., functionalized thiols such as an orthopyridyl disulfide or "OPSS").

With respect to polymeric reagents, those described here and elsewhere can be purchased from commercial sources or prepared from commercially available starting materials. In addition, methods for preparing the polymeric reagents are described in the literature.

The attachment between the IL-7 moiety and the non-peptidic water-soluble polymer can be direct, wherein no intervening atoms are located between the IL-7 moiety and the polymer, or indirect, wherein one or more atoms are located between the IL-7 moiety and the polymer. With respect to the indirect attachment, a "spacer moiety" serves as a linker between the residue of the IL-7 moiety and the water-soluble polymer. The one or more atoms making up the spacer moiety can include one or more of carbon atoms, nitrogen atoms, sulfur atoms, oxygen atoms, and combinations thereof. The spacer moiety can comprise an amide, secondary amine, carbamate, thioether, and/or disulfide group. Nonlimiting examples of specific spacer moieties include those selected from the group consisting of —O—, —S—, —S—S—, —C(O)—, —C(O)—NH—, —NH—C(O)—NH—, —O—C(O)—NH—, —C(S)—, $—CH_2—$, $—CH_2—CH_2—$, $—CH_2—CH_2—CH_2—$, $—CH_2—CH_2—CH_2—CH_2—$, $—O—CH_2—$, $—CH_2—O—$, $—O—CH_2—CH_2—$, $—CH_2—O—CH_2—$, $—CH_2—CH_2—O—$, $—O—CH_2—CH_2—CH_2—$, $—CH_2—O—CH_2—CH_2—$, $—CH_2—CH_2—O—CH_2—$, $—CH_2—CH_2—CH_2—O—$, $—O—CH_2—CH_2—CH_2—CH_2—$, $—CH_2—O—CH_2—CH_2—CH_2—$, $—CH_2—CH_2—O—CH_2—CH_2—$, $—CH_2—CH_2—CH_2—O—CH_2—$, $—CH_2—CH_2—CH_2—CH_2—O—$, $—C(O)—NH—CH_2—$, $—C(O)—NH—CH_2—CH_2—$, $—CH_2—C(O)—NH—CH_2—$, $—CH_2—CH_2—C(O)—NH—$, $—C(O)—NH—CH_2—CH_2—CH_2—$, $—CH_2—C(O)—NH—CH_2—CH_2—$, $—CH_2—CH_2—C(O)—NH—CH_2—$, $—CH_2—CH_2—CH_2—C(O)—NH—$, $—C(O)—NH—CH_2—CH_2—CH_2—CH_2—$, $—CH_2—C(O)—NH—CH_2—CH_2—CH_2—$, $—CH_2—CH_2—C(O)—NH—CH_2—CH_2—$, $—CH_2—CH_2—CH_2—C(O)—NH—CH_2—$, $—CH_2—CH_2—CH_2—C(O)—NH—CH_2—CH_2—$, $—CH_2—CH_2—CH_2—CH_2—C(O)—NH—$, $—C(O)—O—CH_2—$, $—CH_2—C(O)—O—CH_2—$, $—CH_2—CH_2—C(O)—O—CH_2—$, $—C(O)—O—CH_2—CH_2—$, $—NH—C(O)—CH_2—$, $—CH_2—NH—C(O)—CH_2—$, $—CH_2—CH_2—NH—C(O)—CH_2—$, $—NH—C(O)—CH_2—CH_2—$, $—CH_2—NH—C(O)—CH_2—CH_2—$, $—CH_2—CH_2—NH—C(O)—CH_2—CH_2—$, $—C(O)—NH—CH_2—$, $—C(O)—NH—CH_2—CH_2—$, $—O—C(O)—NH—CH_2—$, $—O—C(O)—NH—CH_2—CH_2—$, $—NH—CH_2—$, $—NH—CH_2—CH_2—$, $—CH_2—NH—CH_2—$, $—CH_2—CH_2—NH—CH_2—$, $—C(O)—CH_2—$, $—C(O)—CH_2—CH_2—$, $—CH_2—C(O)—CH_2—$, $—CH_2—CH_2—C(O)—CH_2—$, $—CH_2—CH_2—C(O)—CH_2—CH_2—$, $—CH_2—CH_2—C(O)—$, $—CH_2—CH_2—CH_2—C(O)—NH—CH_2—CH_2—NH—$, $—CH_2—CH_2—CH_2—C(O)—NH—CH_2—CH_2—NH—C(O)—$, $—CH_2—CH_2—CH_2—C(O)—NH—CH_2—CH_2—NH—C(O)—CH_2—$, $—CH_2—CH_2—CH_2—C(O)—NH—CH_2—CH_2—NH—C(O)—CH_2—CH_2—$, $—O—C(O)—NH—[CH_2]_r—(OCH_2CH_2)_j—$, bivalent cycloalkyl group, —O—, —S—, an amino acid, $—N(R^6)—$, and combinations of two or more of any of the foregoing, wherein $R^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—$(CH_2)_{1-6}$—NH—C(O)—, —NH—C(O)—NH—$(CH_2)_{1-6}$—NH—C(O)—, and —O—C(O)—NH—$(CH_2)_{1-6}$—NH—C(O)—, wherein the subscript values following each methylene indicate the number of methylenes contained in the structure, e.g., $(CH_2)_{1-6}$ means that the structure can contain 1, 2, 3, 4, 5 or 6 methylenes. Additionally, any of the above spacer moieties may further include an ethylene oxide oligomer chain comprising 1 to 20 ethylene oxide monomer units [i.e., —$(CH_2CH_2O)_{1-20}$]. That is, the ethylene oxide oligomer chain can occur before or after the spacer moiety, and optionally in between any two atoms of a spacer moiety comprised of two or more atoms. Also, the oligomer chain would not be considered part of the spacer moiety if the oligomer is adjacent to a polymer segment and merely represent an extension of the polymer segment.

Compositions

The conjugates are typically part of a composition. Generally, the composition comprises a plurality of conjugates, preferably although not necessarily, each conjugate is comprised of the same IL-7 moiety (i.e., within the entire composition, only one type of IL-7 moiety is found). In addition, the composition can comprise a plurality of conjugates wherein any given conjugate is comprised of a moiety selected from the group consisting of two or more different IL-7 moieties (i.e., within the entire composition, two or more different IL-7 moieties are found). Optimally, however, substantially all conjugates in the composition (e.g., 85% or more of the plurality of conjugates in the composition) are each comprised of the same IL-7 moiety.

The composition can comprise a single conjugate species (e.g., a monoPEGylated conjugate wherein the single polymer is attached at the same location for substantially all conjugates in the composition) or a mixture of conjugate species (e.g., a mixture of monoPEGylated conjugates where attachment of the polymer occurs at different sites and/or a mixture monPEGylated, diPEGylated and triPEGylated conjugates). The compositions can also comprise other conjugates having four, five, six, seven, eight or more polymers attached to any given moiety having IL-7 activity. In addition, the invention includes instances wherein the composition comprises a plurality of conjugates, each conjugate comprising one water-soluble polymer covalently attached to one IL-7 moiety, as well as compositions comprising two, three, four, five, six, seven, eight, or more water-soluble polymers covalently attached to one IL-7 moiety.

With respect to the conjugates in the composition, the composition will satisfy one or more of the following characteristics at least about 85% of the conjugates in the composition will have from one to eight polymers attached to the IL-7 moiety; at least about 85% of the conjugates in the composition will have from one to seven polymers attached to the IL-7 moiety; at least about 85% of the conjugates in the composition will have from one to five polymers attached to the IL-7 moiety; at least about 85% of the conjugates in the composition will have one to three polymers attached to the IL-7 moiety; at least about 95% of the conjugates in the composition will have from one to two polymers attached to the IL-7 moiety; at least about 95% of the conjugates in the composition will have from three to eight polymers attached to the IL-7 moiety; at least about 95% of the conjugates in the composition will have from two to five seven polymers attached to the IL-7 moiety; at least about 95% of the conjugates in the composition will have from three to six polymers attached to the IL-7 moiety; at least about 95% of the conjugates in the composition will have one polymer attached to the IL-7 moiety; at least about 99% of the conjugates in the composition will have from one to six polymers attached to the IL-7 moiety; at least about 99% of the conjugates in the composition will have from one to four polymers attached to the IL-7 moiety; at least about 99% of the conjugates in the composition will have from one to three polymers attached to the IL-7 moiety; at least about 99% of the conjugates in the composition will have from one to two polymers attached to the IL-7 moiety; and at least about 99% of the conjugates in the composition will have one polymer attached to the IL-7 moiety. It is understood that a reference to a range of polymers, e.g., "from x toy polymers," contemplates a number of polymers x to y inclusive (that is, for example, "from one to three polymers" contemplates one polymer, two polymers and three polymers, "from one to two polymers" contemplates one polymer and two polymers, and so forth). In addition, it is also contemplated that a given conjugate having two or more polymers attached to the IL-7 moiety can have mixtures of stable and releasably attached polymers (wherein at least one polymer is stably attached to the IL-7 moiety and at least one polymer is releasably attached to the IL-7 moiety).

In one or more embodiments, it is preferred that the conjugate-containing composition is free or substantially free of albumin. It is also preferred that the composition is free or substantially free of proteins that do not have IL-7 activity. Thus, it is preferred that the composition is 85%, more preferably 95%, and most preferably 99% free of albumin. Additionally, it is preferred that the composition is 85%, more preferably 95%, and most preferably 99% free of any protein that does not have IL-7 activity. To the extent that albumin is present in the composition, exemplary compositions of the invention are substantially free of conjugates comprising a poly(ethylene glycol) polymer linking a residue of an IL-7 moiety to albumin.

Control of the desired number of polymers for any given moiety can be achieved by selecting the proper polymeric reagent, the ratio of polymeric reagent to the IL-7 moiety, temperature, pH conditions, and other aspects of the conjugation reaction. In addition, reduction or elimination of the undesired conjugates (e.g., those conjugates having four or more attached polymers) can be achieved through purification means.

For example, the polymer-IL-7 moiety conjugates can be purified to obtain/isolate different conjugated species. Specifically, the product mixture can be purified to obtain an average of anywhere from one, two, three, four, five or more PEGs per IL-7 moiety, typically one, two or three PEGs per IL-7 moiety. The strategy for purification of the final conjugate reaction mixture will depend upon a number of factors, including, for example, the molecular weight of the polymeric reagent employed, the particular IL-7 moiety, the desired dosing regimen, and the residual activity and in vivo properties of the individual conjugate(s).

If desired, conjugates having different molecular weights can be isolated using gel filtration chromatography and/or ion exchange chromatography. That is to say, gel filtration chromatography is used to fractionate differently numbered polymer-to-IL-7 moiety ratios (e.g., 1-mer, 2-mer, 3-mer, and so forth, wherein "1-mer" indicates 1 polymer to IL-7 moiety, "2-mer" indicates two polymers to IL-7 moiety, and so on) on the basis of their differing molecular weights (where the difference corresponds essentially to the average molecular weight of the water-soluble polymer portion). For example, in an exemplary reaction where a 35,000 Dalton protein is randomly conjugated to a polymeric reagent having a molecular weight of about 20,000 Daltons, the resulting reaction mixture may contain unmodified protein (having a molecular weight of about 35,000 Daltons), monoPEGylated protein (having a molecular weight of about 55,000 Daltons), diPEGylated protein (having a molecular weight of about 75,000 Daltons), and so forth.

While this approach can be used to separate PEG and other polymer-IL-7 moiety conjugates having different molecular weights, this approach is generally ineffective for separating positional isoforms having different polymer attachment sites within the IL-7 moiety. For example, gel filtration chromatography can be used to separate from each other mixtures of PEG 1-mers, 2-mers, 3-mers, and so forth, although each of the recovered conjugate compositions may contain PEG(s) attached to different reactive groups (e.g., lysine residues) within the IL-7 moiety.

Gel filtration columns suitable for carrying out this type of separation include Superdex™ and Sephadex™ columns available from GE Healthcare (Buckinghamshire, UK). Selection of a particular column will depend upon the desired fractionation range desired. Elution is generally carried out using a suitable buffer, such as phosphate, acetate, or the like. The collected fractions may be analyzed by a number of different methods, for example, (i) absorbance at 280 nm for protein content, (ii) dye-based protein analysis using bovine serum albumin (BSA) as a standard, (iii) iodine testing for PEG content (Sims et al. (1980) *Anal. Biochem,* 107:60-63), (iv) sodium dodecyl sulfate polyacrylamide gel electrophoresis (SDS PAGE), followed by staining with barium iodide, and (v) high performance liquid chromatography (HPLC).

Separation of positional isoforms is carried out by reverse phase chromatography using a reverse phase-high performance liquid chromatography (RP-HPLC) using a suitable column (e.g., a C18 column or C3 column, available commercially from companies such as Amersham Biosciences or Vydac) or by ion exchange chromatography using an ion exchange column, e.g., a Sepharose™ ion exchange column available from GE Healthcare. Either approach can be used to separate polymer-active agent isomers having the same molecular weight (i.e., positional isoforms).

The compositions are preferably substantially free of proteins that do not have IL-7 activity. In addition, the compositions preferably are substantially free of all other noncovalently attached water-soluble polymers. In some circumstances, however, the composition can contain a mixture of polymer-IL-7 moiety conjugates and unconjugated IL-7 moiety.

Optionally, the composition of the invention further comprises a pharmaceutically acceptable excipient. If desired, the pharmaceutically acceptable excipient can be added to a conjugate to form a composition.

Exemplary excipients include, without limitation, those selected from the group consisting of carbohydrates, inorganic salts, antimicrobial agents, antioxidants, surfactants, buffers, acids, bases, amino acids, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, cyclodextrins, and the like.

The excipient can also include an inorganic salt or buffer such as citric acid, acetic acid, sodium chloride, potassium chloride, sodium sulfate, potassium nitrate, sodium phosphate monobasic, sodium phosphate dibasic, and combinations thereof.

The composition can also include an antimicrobial agent for preventing or deterring microbial growth. Nonlimiting examples of antimicrobial agents suitable for one or more embodiments of the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the conjugate or other components of the preparation. Suitable antioxidants for use in one or more embodiments of the present invention include, for example, ascorbyl palmitate, butylated hydroxyanisole, butylated hydroxytoluene, hypophosphorous acid, monothioglycerol, propyl gallate, sodium bisulfate, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Florham Park, NJ); sorbitan esters; lipids, such as phospholipids such as lecithin and other phosphatidylcholines, phosphatidylethanolamines (although preferably not in liposomal form), fatty acids and fatty esters; steroids, such as cholesterol; and IL-7lating agents, such as EDTA, zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

One or more amino acids can be present as an excipient in the compositions described herein. Exemplary amino acids in this regard include arginine, lysine and glycine.

The amount of the conjugate (i.e., the conjugate formed between the active agent and the polymeric reagent) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, NJ (1998), and Kibbe, A. H., Handbook of Pharmaceutical Excipients, $3^{rd}$ Edition, American Pharmaceutical Association, Washington, D.C., 2000.

The compositions encompass all types of formulations and in particular those that are suited for injection, e.g., powders or lyophilates that can be reconstituted as well as liquids. Examples of suitable diluents for reconstituting solid compositions prior to injection include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned.

In one or more embodiments, the composition can also be a hydrogel. Exemplary hydrogels include those that include poly(ethylene glycol) (in unconjugated form), such as those described in Zustiak et al. (2010) *Biomacromolecules* 11(5): 1348-1357.

The compositions of one or more embodiments are typically, although not necessarily, administered via injection and are therefore generally hydrogels, liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, intratumorally, peritumorally, intraperitoneally, subcutaneous, intra-arterial, and so forth.

The invention also provides a method for administering a conjugate as provided herein to a patient suffering from a condition that is responsive to treatment with conjugate. The method comprises administering to a patient, generally via injection, a therapeutically effective amount of the conjugate (preferably provided as part of a pharmaceutical composition). As previously described, the conjugates can be injected (e.g., intramuscularly, subcutaneously and parenterally). Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The method of administering the conjugate (preferably provides as part of a pharmaceutical composition) can optionally be conducted so as to localize the conjugate to a specific area. For example, the liquid, gel and solid formulations comprising the conjugate could be surgically implanted in a diseased area (such as in a tumor, near a tumor, in an inflamed area, and near an inflamed area). Conveniently, organs and tissue can also be imaged in order to ensure the desired location is better exposed to the conjugate.

The method of administering may be used to treat any condition that can be remedied or prevented by administration of the conjugate. Those of ordinary skill in the art appreciate which conditions a specific conjugate can effectively treat. For example, the conjugates can be used either alone or in combination with other pharmacotherapy to treat patients suffering from immune deficiencies and in accelerating the natural reconstitution of the immune system that occurs, for example, after diseases or treatments that are immunosuppressive in nature. For example, the conjugates can be used to treat viral infections, immune disorders, and to enhance the growth (including proliferation) of specific cell types. Moreover, conjugates can be used in the treatment patients suffering from a cancer, such as bladder cancer, lung cancer, brain cancer, breast cancer, skin cancer, and prostate cancer. Advantageously, the conjugate can be administered to the patient prior to, simultaneously with, or after administration of another active agent. For example, the conjugate may be used as part of an immunotherapy-involved approached for treating a patient suffering from cancer, wherein the conjugate is administered to the patient prior to, simultaneously with, or after administration of another immunotherapeutic drug used in the treatment of individuals suffering from cancer.

The actual dose to be administered will vary depending upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day. A given dose can be periodically administered up until, for example, the clinician determines an appropriate endpoint (e.g., cure, regression, partial regression, and so forth) is achieved.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

EXPERIMENTAL

The practice of the invention will employ, unless otherwise indicated, conventional techniques of organic synthesis, biochemistry, protein purification and the like, which are within the skill of the art. Such techniques are fully explained in the literature. See, for example, *J. March, Advanced Organic Chemistry*: Reactions Mechanisms and Structure, 4th Ed. (New York: Wiley-Interscience, 1992), supra.

In the following examples, efforts have been made to ensure accuracy with respect to numbers used (e.g., amounts, temperatures, etc.) but some experimental error and deviation should be taken into account. Unless indicated otherwise, temperature is in degrees C. and pressure is at or near atmospheric pressure at sea level. Each of the following examples is considered to be instructive to one of ordinary skill in the art for carrying out one or more of the embodiments described herein.

An aqueous solution ("stock solution") comprising recombinant IL-7 ("rhIL-7") corresponding to the amino acid sequence of SEQ ID NO: 1 was prepared for use in the examples.

SDS-PAGE Analysis

Samples were analyzed by sodium dodecyl sulfate-polyacrylamide gel electrophoresis (SDS-PAGE) using Invitrogen gel electrophoresis system (XCell SureLock Mini-Cell). Samples were mixed with sample buffer. The prepared samples were then loaded onto a NuPAGE Novex 4-12% polyacrylamide precast gel and run for approximately thirty minutes.

RP-HPLC Analysis

Reversed-phase chromatography (RP-HPLC) analysis was performed on an Agilent 1200 HPLC system (Agilent). Samples were analyzed using a Poroshell 300SB-C3 column (2.1×75 mm, Agilent) at 60° C. The mobile phases are 0.1% TFA/$H_2O$ (A) and 0.1% TFA/$CH_3CN$ (B). The flow rate for the column was 0.5 ml/minute. The eluted protein and PEG-protein conjugates were detected using UV at 280 nm.

Example 1

PEGylation of IL-7 with Branched mPEG-N-Hydroxysuccinimide Derivative, 20 kDa

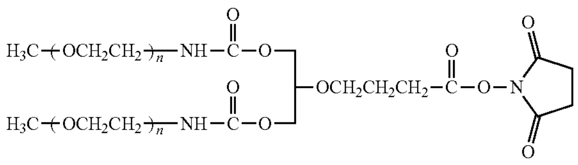

Branched mPEG-N-Hydroxysuccinimide Derivative, 20 kDa, ("mPEG2-NHS")

mPEG2-NHS, 20 kDa, stored at −20° C. under argon, was warmed to ambient temperature. A ten- to fifty-fold excess (relative to the amount of IL-7 in a measured aliquot of the stock IL-7 solution) of the warmed mPEG2-NHS was dissolved in 2 mM HCl to form a 10% reagent solution. The 10% reagent solution was quickly added to the aliquot of stock IL-7 solution (0.5 mg/ml in 20 mM Tris, 50 mM NaCl, pH7.8) and mixed well. To allow for coupling of the mPEG2-NHS to IL-7 via an amide linkage, the reaction solution was placed on a Slow Speed Lab Rotator for two hours at room temperature and then, overnight at 4° C. The reaction was quenched with 25 mM glycine solution. The conjugate was characterized by both SDS-PAGE and RP-HPLC.

FIG. 1 shows the chromatogram following the RP-HPLC analysis of the conjugate solution from using ten-fold excess of PEG. The PEGylation reaction yielded 44% mono-conjugate (one PEG attached to IL-7), 35% di-conjugate (two PEGs attached to IL-7) and 14% tri-conjugate (three PEGs attached to IL-7) species. There was only 7% unreacted IL-7 remaining in the solution.

Figure 2:
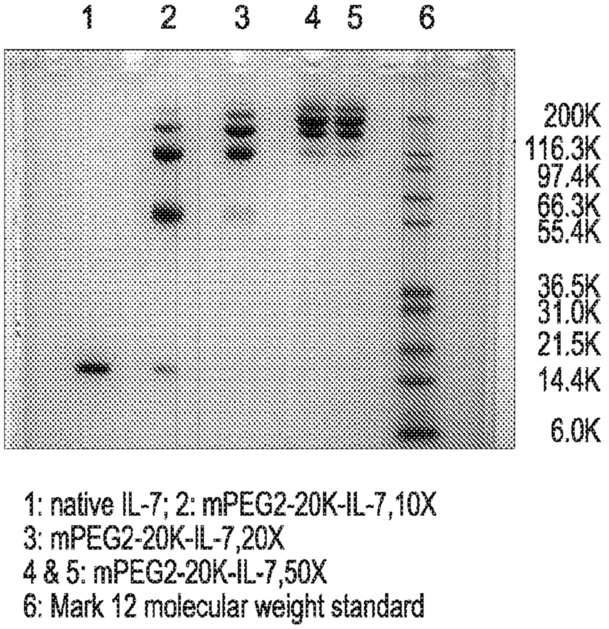
FIG. 2 is an image of an SDS-PAGE gel of the conjugation reaction mixtures of IL-7 with varying amounts of mPEG2-NHS, 20 kDa as described in Example 1.

FIG. 2 shows the SDS gel results of PEGylation at different mPEG2-NHS, 20 kDa concentrations (i.e., 10×, 20×, and 50× excess).

Example 2

PEGylation of IL-7 with Branched mPEG-N-Hydroxysuccinimide Derivative, 40 kDa

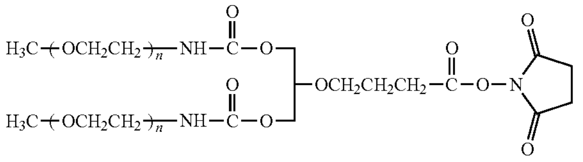

Branched mPEG-N-Hydroxysuccinimide Derivative, 40 kDa, ("mPEG2-NHS")

mPEG2-NHS, 40 kDa, stored at −20° C. under argon, was warmed to ambient temperature. A ten- to fifty-fold excess (relative to the amount of IL-7 in a measured aliquot of the stock IL-7 solution) of the warmed mPEG2-NHS was dissolved in 2 mM HCl to form a 10% reagent solution. The 10% reagent solution was quickly added to the aliquot of stock IL-7 solution (0.5 mg/ml in 20 mM Tris, 50 mM NaCl, pH7.8) and mixed well. To allow for coupling of the mPEG2-NHS to IL-7 via an amide linkage, the reaction solution was placed on a Slow Speed Lab Rotator for two hours at room temperature and then, overnight at 4° C. The reaction was quenched with 25 mM glycine solution. The conjugate was characterized by both SDS-PAGE and RP-HPLC.

Figure 3:
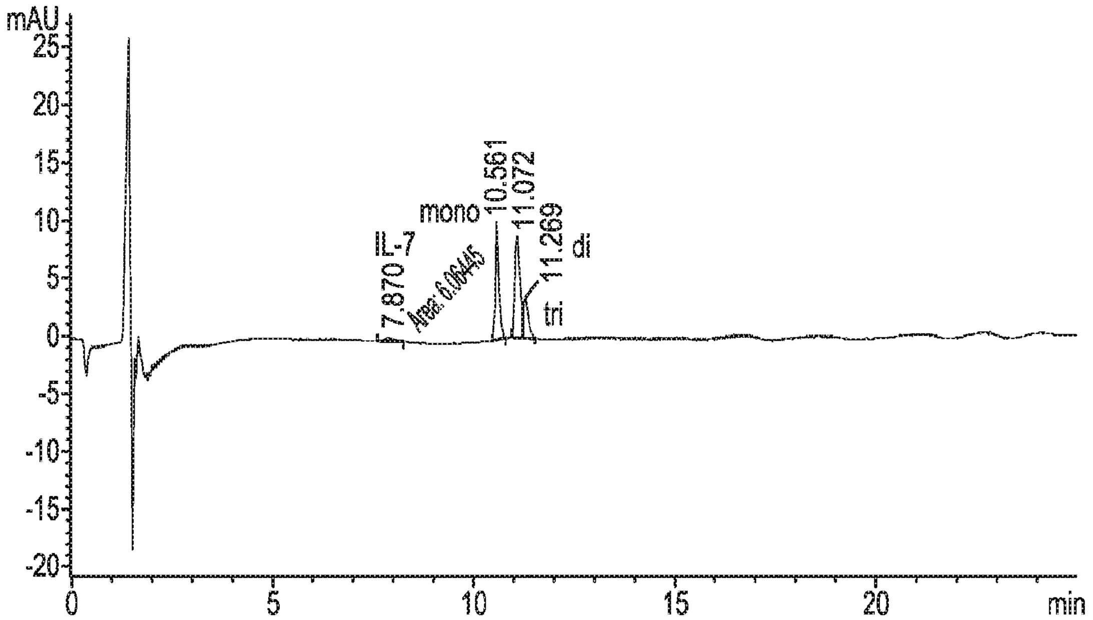
FIG. 3 is a plot of the RP-HPLC analysis of mPEG2-NHS, 40 kDa-IL-7 conjugate solution prepared as described in Example 2.

FIG. 3 shows the chromatogram following the RP-HPLC analysis of the conjugate solution from using ten-fold excess of PEG. The PEGylation reaction yielded 36% mono-conjugate, 44% di-conjugate and 17% tri-conjugate species. There was only 3% unreacted IL-7 remaining in the solution.

Figure 4:
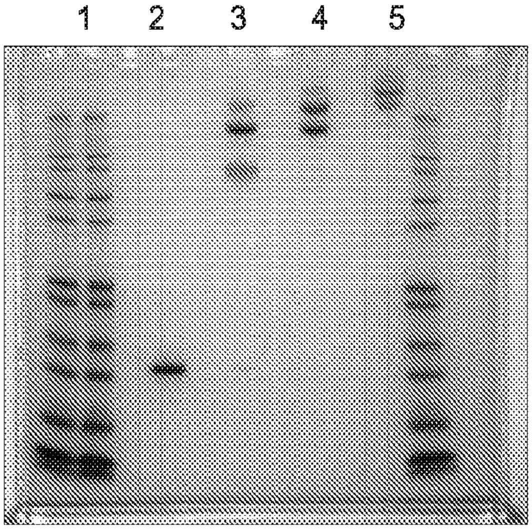
FIG. 4 is an image of an SDS-PAGE gel of the conjugation reaction mixtures of IL-7 with varying amounts of mPEG2-NHS, 40 kDa as described in Example 2.

FIG. 4 shows the SDS gel results of PEGylation at different mPEG2-NHS, 40 kDa concentrations (i.e., 10×, 20×, and 50× excess).

Example 3

PEGylation of IL-7 with 9-Hydroxymethyl-2,7-Di [mPEG(10,000)-Carboxamido] Fluorene-N-Hydroxysuccinimide Derivative, 20 kDa

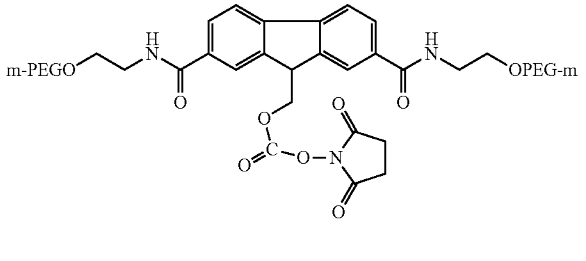

Branched mPEG-FMOC—N-Hydroxysuccinimide Derivative, 20 kDa, ("C2-PEG2-FMOC-NHS")

C2-PEG2-FMOC-NHS, 20 kDa, stored at −20° C. under argon, was warmed to ambient temperature. A ten- to fifty-fold excess (relative to the amount of IL-7 in a measured aliquot of the stock IL-7 solution) of the warmed C2-PEG2-FMOC-NHS was dissolved in 2 mM HCl to form a 10% reagent solution. The 10% reagent solution was quickly added to the aliquot of stock IL-7 solution (0.5 mg/ml in 20 mM Tris, 50 mM NaCl, pH7.8) and mixed well. To allow for coupling of the C2-PEG2-FMOC-NHS to IL-7 via a carbamate linkage, the reaction solution was placed on a Slow Speed Lab Rotator for two hours at room temperature and then, overnight at 4° C. The reaction was quenched with 25 mM glycine solution. The conjugate was characterized by both SDS-PAGE and RP-HPLC.

Figure 5:
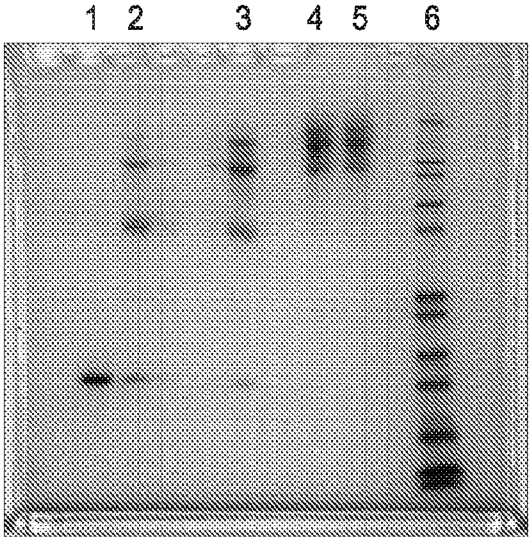
FIG. 5 is an image of an SDS-PAGE gel of the conjugation reaction mixtures of IL-7 with varying amounts of C2-PEG2-FMOC-NHS, 20 kDa as described in Example 3.

FIG. 5. shows the SDS gel result of PEGylation scoutings. As indicated in the gel below, the dominant species with ten-fold excess of the reagent was the mono-conjugate (43%), while the dominant species with twenty-fold excess of the reagent was the di-conjugate (40%), and the dominant species with fifty-fold excess of the reagent was the tri-conjugate (47%).

Using this same approach, other conjugates can be prepared using C2-PEG2-FMOC-NHS having other weight average molecular weights.

Example 4

PEGylation of IL-7 with Linear mPEG-Succinimidyl α-Methylbutanoate Derivative, 30 kDa

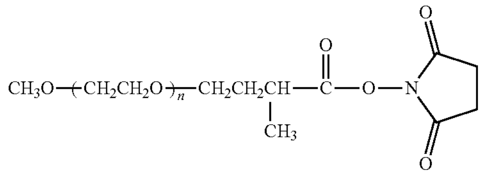

Linear mPEG-Succinimidyl α-Methylbutanoate Derivative, 30 kDa ("mPEG-SMB")

mPEG-SMB, 30 kDa, stored at −20° C. under argon, is warmed to ambient temperature. A twenty-fold excess (relative to the amount of IL-7 in a measured aliquot of the stock IL-7 solution) of the warmed mPEG-SMB is dissolved in 2 mM HCl to form a 10% reagent solution. The 10% reagent solution was quickly added to the aliquot of stock IL-7 solution (0.5 mg/ml in sodium phosphate buffer, pH 7.5) and mixed well. After the addition of the mPEG-SMB, the pH of the reaction mixture is determined and adjusted to 7.5 using conventional techniques. To allow for coupling of the mPEG-SMB to IL-7 via an amide linkage, the reaction solution is placed on a Slow Speed Lab Rotator overnight to facilitate conjugation at room temperature. The reaction is quenched with Glycine solution. The conjugate solution is characterized by HPLC and SDS-PAGE.

Using this same approach, other conjugates can be prepared using mPEG-SMB having other weight average molecular weights.

Example 5

PEGylation of IL-7 with Linear mPEG-Butyraldehyde Derivative, 20 kDa

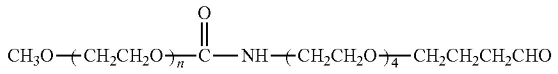

Linear mPEG-Butyraldehyde Derivative, 20 kDa ("mPEG-ButyrALD")

mPEG-ButyrALD, 20 kDa, stored at −20° C. under argon, is warmed to ambient temperature. A thirty-fold excess (relative to the amount of IL-7 in a measured aliquot of the stock IL-7) of the warmed mPEG-Butry ALD is dissolved in Milli-Q $H_2O$ to form a 10% reagent solution. The 10% reagent solution is quickly added to the aliquot of stock IL-7 solution (0.5 mg/ml in sodium acetate buffer, pH 5.5) and mixed well. After the addition of the mPEG-ButryALD for thirty minutes, a reducing agent, sodium cyanoborohydride, was then added to make 10 mM $NaCNBH_3$. The reaction solution is placed on a Slow Speed Lab Rotator overnight to facilitate conjugation at room temperature. The reaction is quenched with acetic acid to pH 4. The conjugate solution is characterized by HPLC and SDS-PAGE.

The aldehyde group of mPEG-ButyrALD can react with the primary amines associated with IL-7 and covalently bond to them via secondary amine upon reduction by a reducing reagent such as sodium cyanoborohydride. Because the PEGylation reaction is carried at pH 5.5, attachment of the PEG derivative to IL-7 is more selective to the N-terminal.

Using this same approach, other conjugates can be prepared using linear mPEG-ButyrALD having other weight average molecular weights.

Example 6

PEGylation of IL-7 with Branched mPEG-Butyraldehyde Derivative, 40 kDa

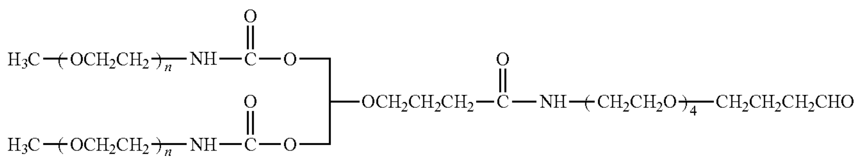

Branched mPEG-Butyraldehyde Derivative, 40 kDa ("mPEG2-ButyrALD")

mPEG2-ButyrALD, 40 kDa, stored at −20° C. under argon, is warmed to ambient temperature. A thirty-fold excess (relative to the amount of IL-7 in a measured aliquot of the stock IL-7) of the warmed mPEG2-ButryALD is dissolved in Milli-Q $H_2O$ to form a 10% reagent solution. The 10% reagent solution is quickly added to the aliquot of stock IL-7 solution (0.5 mg/ml in sodium phosphate buffer, pH 6.0) and mixed well. After the addition of the mPEG2-ButryALD for thirty minutes, a reducing agent, sodium cyanoborohydride, is then added to make 10 mM $NaCNBH_3$. The reaction solution is placed on a Slow Speed Lab Rotator overnight to facilitate conjugation at room temperature. The reaction is quenched with acetic acid to pH 4. The conjugate solution is characterized by HPLC and SDS-PAGE analysis.

The aldehyde group of mPEG2-ButyrALD can react with the primary amines associated with IL-7 and covalently bond to them via secondary amine upon reduction by a reducing reagent such as sodium cyanoborohydride. Because the PEGylation reaction is carried at pH 6.0, attachment of the PEG derivative to IL-7 is more selective to the N-terminal.

Using this same approach, other conjugates can be prepared using branched mPEG2-ButyrALD having other weight average molecular weights.

Example 7

PEGylation of IL-7 with 9-Hydroxymethyl-4-(mPEG(20,000)-Carboxyamide)-7-(3-(mPEG(20,000))Carbamoyl-Propyl)-Fluorene-N-Hydroxysuccinimidyl Carbonate, 40 kDa

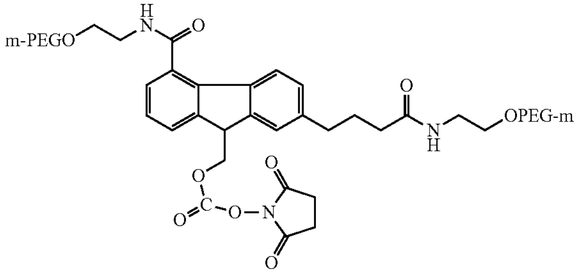

Branched mPEG-FMOC—N-Hydroxysuccinimide Derivative, 40 kDa, ("CAC-PEG2-FMOC-NHS")

CAC-PEG2-FMOC-NHS, 40 kDa, stored at −20° C. under argon, is warmed to ambient temperature. A ten- to fifty-fold excess (relative to the amount of IL-7 in a measured aliquot of the stock IL-7 solution) of the warmed CAC-PEG2-FMOC-NHS is dissolved in 2 mM HCl to form a 10% reagent solution. The 10% reagent solution is quickly added to the aliquot of stock IL-7 solution (0.5 mg/ml in sodium phosphate buffer, pH 7.5) and mixed well. The reaction solution is placed on a Slow Speed Lab Rotator (RotoMix) at room temperature for two hours initially, and then at 4° C. overnight. The reaction is quenched by the addition of 1M acetic acid to lower the pH to 5. The conjugate solution is characterized by SDS-PAGE and HPLC.

Due to the releasable linkage in the PEG structure, the PEGs are releasable from the PEG-IL-7 conjugates under physiological condition.

Using this same approach, other conjugates can be prepared using CAC-PEG2-FMOC-NHS having other weight average molecular weights.

Example 8

PEGylation of IL-7 with 9-Hydroxymethyl-[4-Carboxamido M-PEG (20,000)-7-Amidoglutaric Amide M-PEG(20,000)] Fluorene-N-Hydroxysuccinimide Derivative, 40 kDa

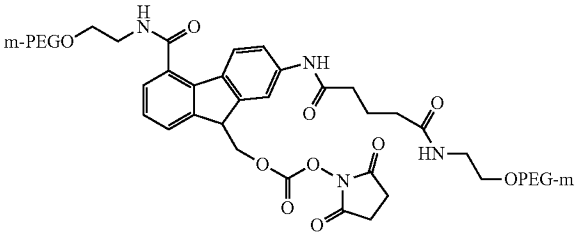

Branched mPEG-FMOC—N-Hydroxysuccinimide Derivative, 40 kDa, ("CG-PEG2-FMOC-NHS")

CG-PEG2-FMOC-NHS, 40 kDa, stored at −20° C. under argon, is warmed to ambient temperature. A ten- to fifty-fold excess (relative to the amount of IL-7 in a measured aliquot of the stock IL-7 solution) of the warmed CG-PEG2-FMOC-NHS is dissolved in 2 mM HCl to form a 10% reagent solution. The 10% reagent solution is quickly added to the aliquot of stock IL-7 solution (0.5 mg/ml in sodium phosphate buffer, pH 7.5) and mixed well. The reaction solution is placed on a Slow Speed Lab Rotator (RotoMix) at room temperature for two hours initially, and then at 4° C. overnight. The reaction is quenched by the addition of 1M acetic acid to lower the pH to 5. The conjugate solution is characterized by SDS-PAGE and HPLC.

Due to the degradable linkage in the PEG structure, the PEGs are releasable from the PEG-IL-7 conjugates under physiological condition.

Using this same approach, other conjugates can be prepared using CG-PEG2-FMOC-NHS having other weight average molecular weights.

```
                                          SEQ ID NO: 1
       10         20         30         40
MDCDIEGKDG KQYESVLMVS IDQLLDSMKE IGSNCLNNEF

       50         60         70         80
NFFKRHICDA NKEGMFLFRA ARKLRQFLKM NSTGDFDLHL

       90        100        110        120
LKVSEGTTIL LNCTGQVKGR KPAALGEAQP TKSLEENKSL

      130        140        150
KEQKKLNDLC FLKRLLQEIK TCWNKILMGT KEH
```

-continued

SEQ ID NO: 2

```
        10         20         30         40
DCDIEGKDGK QYESVLMVSI DQLLDSMKEI GSNCLNNEFN

        50         60         70         80
FFKRHICDAN KEGMFLFRAA RKLRQFLKMN STGDFDLHLL

        90        100        110        120
KVSEGTTILL NCTGQVKGRK PAALGEAQPT KSLEENKSLK

       130        140        150
EQKKLNDLCF LKRLLQEIKT CWNKILMGTK EH
```

SEQ ID NO: 3

```
        10         20         30         40
DCDIEGKDGK QYESVLMVSI DQLLDSMKEI GSNCLNNEFN

        50         60         70         80
FFKRHICDAN KEGMFLFRAA RKLRQFLKMN STGDFDLHLL

        90        100        110        120
KVSEGTTILL NCTGQEENKS LKEQKKLNDL CFLKRLLQEI

       130
KTCWNKILMG TKEH
```

SEQ ID NO: 4

```
        10         20         30         40
DCDIEGKDGK QYESVLMVSI DQLLDSMKEI GSNCLNNEFN

        50         60         70         80
FFKRHICDAN KEGMFLFRAA RKLRQFLKMN STGDFDLHLL

        90        100        110        120
KVSEGTTILL KEQKKLNDLC FLKRLLQEIK TCWNKILMGT

KEH
```

-continued

SEQ ID NO: 5

```
        10         20         30         40
DCDIEGKDGK QYESVLMVSI DQLLDSMKEI GSNCLNNEFN

        50         60         70         80
FFKRHICDAN KVKGRKPAAL GEAQPTKSLE ENESLKEQKK

        90        100
LNDLCFLKRL LQEIKTCWNK ILMGTKEH
```

SEQ ID NO: 6

```
        10         20         30         40
DCDIEGKDGK QYESVLMVSI DQLLDSMKEI GSNCLNNEFN

        50         60         70         80
FFKRHICDAN KEENESLKEQ KKLNDLCFLK RLLQEIKTCW

        90
NKILMGTKEH
```

SEQ ID NO: 7

```
        10         20         30         40
DCDIEGKDGK QYESVLMVSI DQLLVKGRKP AALGEAQPTK

        50         60         70         80
SLEENESLKE QKKLNDLCFL KRLLQEIKTC WNKILMGTKE

        90        100        110        120
H
```

SEQ ID NO: 8

```
        10         20         30         40
DCDIEGKDGK QYESVLMVSI DQLLEENKSL KEQKKLNDLC

        50         60
FLKRLLQEIK TCWNKILMGT KEH
```

What is claimed is:

1. A conjugate comprising an interleukin-7 (IL-7) moiety covalently attached to a poly (ethylene glycol) polymer at an amino group of the IL-7 moiety via an amine linkage, the conjugate comprising a structure:

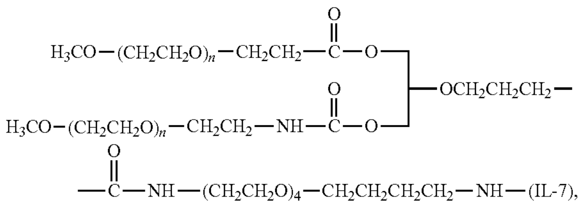

wherein:

each (n) is independently an integer having a value of from 2 to 4000;

IL-7 is an IL-7 moiety, and wherein the conjugate possesses a measurable degree of IL-7 bioactivity.

2. The conjugate of claim 1, wherein for each structure, the poly (ethylene glycol) polymer has a weight-average molecular weight in a range of from about 500 Daltons to about 100,000 Daltons.

3. The conjugate of claim 1, wherein one, two, three or four poly (ethylene glycol) polymers are attached to the IL-7 moiety.

4. The conjugate of claim 3, wherein one, two or three poly (ethylene glycol) polymers are attached to the IL-7 moiety.

5. The conjugate of claim 4, wherein one or two poly (ethylene glycol) polymers are attached to the IL-7 moiety.

6. The conjugate of claim 5, wherein one poly (ethylene glycol) polymer is attached to the IL-7 moiety.

7. The conjugate of claim 1, wherein the IL-7 moiety has an amino acid sequence selected from the group consisting of SEQ ID NO: 1; SEQ ID NO: 2; SEQ ID NO: 3; SEQ ID NO: 4; SEQ ID NO: 5; SEQ ID NO: 6; SEQ ID NO: 7; and SEQ ID NO: 8.

8. A pharmaceutical composition comprising the conjugate of claim 1 and a pharmaceutically acceptable excipient.

9. The conjugate of claim 1, wherein the weight average molecular weight of the poly (ethylene glycol) polymer comprised in the conjugate is from about 20,000 Daltons to about 85,000 Daltons.

10. The conjugate of claim 1, wherein the weight average molecular weight of the poly (ethylene glycol) polymer is about 20,000 Daltons or about 40,000 Daltons.

11. The conjugate of claim 1, wherein the poly (ethylene glycol) polymer is covalently attached to an amino group at the N-terminus of the IL-7 moiety.

* * * * *

SEQUENCE LISTING

```
<160> NUMBER OF SEQ ID NOS: 8

<210> SEQ ID NO 1
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
    50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125

Leu Cys Phe Leu Lys Arg Leu Leu Gln Glu Ile Lys Thr Cys Trp Asn
```

```
    130                 135                 140

Lys Ile Leu Met Gly Thr Lys Glu His
145                 150


<210> SEQ ID NO 2
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150


<210> SEQ ID NO 3
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Glu
                85                  90                  95

Glu Asn Lys Ser Leu Lys Glu Gln Lys Lys Leu Asn Asp Leu Cys Phe
            100                 105                 110

Leu Lys Arg Leu Leu Gln Glu Ile Lys Thr Cys Trp Asn Lys Ile Leu
```

```
        115                 120                 125

Met Gly Thr Lys Glu His
    130


<210> SEQ ID NO 4
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Lys Glu Gln Lys Lys Leu
                85                  90                  95

Asn Asp Leu Cys Phe Leu Lys Arg Leu Leu Gln Glu Ile Lys Thr Cys
            100                 105                 110

Trp Asn Lys Ile Leu Met Gly Thr Lys Glu His
        115                 120


<210> SEQ ID NO 5
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Val Lys Gly Arg Lys Pro Ala Ala Leu Gly Glu Ala Gln
    50                  55                  60

Pro Thr Lys Ser Leu Glu Glu Asn Glu Ser Leu Lys Glu Gln Lys Lys
65                  70                  75                  80

Leu Asn Asp Leu Cys Phe Leu Lys Arg Leu Leu Gln Glu Ile Lys Thr
                85                  90                  95

Cys Trp Asn Lys Ile Leu Met Gly Thr Lys Glu His
            100                 105


<210> SEQ ID NO 6
<211> LENGTH: 90
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 6

Asp Cys Asp Ile Glu Gly Lys Asp Gly Lys Gln Tyr Glu Ser Val Leu
1 5 10 15

Met Val Ser Ile Asp Gln Leu Leu Asp Ser Met Lys Glu Ile Gly Ser
20 25 30

Asn Cys Leu Asn Asn Glu Phe Asn Phe Phe Lys Arg His Ile Cys Asp
35 40 45

Ala Asn Lys Glu Glu Asn Glu Ser Leu Lys Glu Gln Lys Lys Leu Asn
50 55 60

Asp Leu Cys Phe Leu Lys Arg Leu Leu Gln Glu Ile Lys Thr Cys Trp
65 70 75 80

Asn Lys Ile Leu Met Gly Thr Lys Glu His
85 90

<210> SEQ ID NO 7
<211> LENGTH: 81
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 7

Asp Cys Asp Ile Glu Gly Lys Asp Gly Lys Gln Tyr Glu Ser Val Leu
1 5 10 15

Met Val Ser Ile Asp Gln Leu Leu Val Lys Gly Arg Lys Pro Ala Ala
20 25 30

Leu Gly Glu Ala Gln Pro Thr Lys Ser Leu Glu Glu Asn Glu Ser Leu
35 40 45

Lys Glu Gln Lys Lys Leu Asn Asp Leu Cys Phe Leu Lys Arg Leu Leu
50 55 60

Gln Glu Ile Lys Thr Cys Trp Asn Lys Ile Leu Met Gly Thr Lys Glu
65 70 75 80

His

<210> SEQ ID NO 8
<211> LENGTH: 63
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 8

Asp Cys Asp Ile Glu Gly Lys Asp Gly Lys Gln Tyr Glu Ser Val Leu
1 5 10 15

Met Val Ser Ile Asp Gln Leu Leu Glu Glu Asn Lys Ser Leu Lys Glu
20 25 30

Gln Lys Lys Leu Asn Asp Leu Cys Phe Leu Lys Arg Leu Leu Gln Glu
35 40 45

Ile Lys Thr Cys Trp Asn Lys Ile Leu Met Gly Thr Lys Glu His
50 55 60